US012708572B2

(12) United States Patent
Kroutilova et al.

(10) Patent No.: US 12,708,572 B2
(45) Date of Patent: Aug. 18, 2026

(54) BULKY NONWOVEN FABRIC WITH ENHANCED COMPRESSIBILITY AND RECOVERY

(71) Applicants: REIFENHAUSER GMBH & CO. KG MASCHINENFABRIK, Troisdorf (DE); PFNONWOVENS CZECH S.R.O, Znojmo (CZ); PFN-GIC A.S., Znojmo (CZ)

(72) Inventors: Jana Kroutilova, Bozice (CZ); Michael Maas, Rösrath (DE); Zdenek Mecl, Novy Saldorf—Sedlesovice (CZ); Tobias Wagner, Cologne (DE); Frantisek Klaska, Slavkov u Brna (CZ); Pavlina Kasparkova, Znojmo (CZ)

(73) Assignees: REIFENHÄUSER GMBH & CO. KG MASCHINENFABRIK, Troisdorf (DE); PFNONWOVENS CZECH S.R.O, Znojmo (CZ); PFN—GIC A.S., Znojmo (CZ)

( * ) Notice: Subject to any disclaimer, the term of this patent is extended or adjusted under 35 U.S.C. 154(b) by 1173 days.

(21) Appl. No.: 17/295,184

(22) PCT Filed: Nov. 22, 2019

(86) PCT No.: PCT/CZ2019/050053

§ 371 (c)(1),
(2) Date: May 19, 2021

(87) PCT Pub. No.: WO2020/103964

PCT Pub. Date: May 28, 2020

(65) Prior Publication Data

US 2022/0008263 A1 Jan. 13, 2022

(30) Foreign Application Priority Data

Nov. 23, 2018 (CZ) .................................... 2018-647

(51) Int. Cl.
*A61F 13/538* (2006.01)
*A61F 13/15* (2006.01)
(Continued)

(52) U.S. Cl.
CPC ...... *A61F 13/538* (2013.01); *A61F 13/15203* (2013.01); *B01J 20/262* (2013.01);
(Continued)

(58) Field of Classification Search
CPC ...... A61F 13/15; A61F 13/538; A61F 13/511; A61F 13/514; A61F 13/53; A61F 13/534;
(Continued)

(56) References Cited

U.S. PATENT DOCUMENTS 4,981,749 A 1/1991 Kubo et al.
5,855,784 A 1/1999 Pike et al.
(Continued)

FOREIGN PATENT DOCUMENTS

BR 112021009926 B1 7/2025
CN 113166989 A 7/2021
(Continued)

OTHER PUBLICATIONS

International Search Report dated Mar. 12, 2020 in connection with PCT International Patent Application No. PCT/CZ2019/050053.
(Continued)

*Primary Examiner* — Michele Kidwell
(74) *Attorney, Agent, or Firm* — Amster, Rothstein & Ebenstein LLP

(57) ABSTRACT

A nonwoven fabric and a method of production of said nonwoven fabric are disclosed, wherein the nonwovens fabric comprises at least one layer, said layer comprising endless filaments, —which comprise at least a first polymeric material (A) and a second polymeric material (B) having its melting point lower than the first polymeric
(Continued)

material A, —wherein the second polymeric material (B) extends in the longitudinal direction of the filament and forms at least a part of the surface of the filament and—the at least one layer of endless filaments comprises filament-to-filament bonds formed of the second polymeric material (B), wherein all components of the filaments are arranged across the cross-section of the filament in a non-crimpable configuration and the nonwoven fabric has a structural softness of at least 80 ($m^4$ $mm^2$ $g^{-2}$).

9 Claims, 11 Drawing Sheets

(51) Int. Cl.

| | |
|---|---|
| ***A61F 13/53*** | (2006.01) |
| ***B01J 20/26*** | (2006.01) |
| ***B01J 20/28*** | (2006.01) |
| ***C08L 67/04*** | (2006.01) |
| ***D01D 5/30*** | (2006.01) |
| ***D01D 10/00*** | (2006.01) |
| ***D01F 8/04*** | (2006.01) |
| ***D04H 3/007*** | (2012.01) |
| ***D04H 3/011*** | (2012.01) |
| ***D04H 3/147*** | (2012.01) |
| ***D04H 3/16*** | (2006.01) |

(52) U.S. Cl.
CPC ......... *B01J 20/28028* (2013.01); *C08L 67/04* (2013.01); *D01D 5/30* (2013.01); *D01D 10/00* (2013.01); *D01F 8/04* (2013.01); *D04H 3/007* (2013.01); *D04H 3/011* (2013.01); *D04H 3/147* (2013.01); *D04H 3/16* (2013.01); *A61F 2013/15357* (2013.01); *A61F 2013/15406* (2013.01); *A61F 2013/53016* (2013.01); *A61F 2013/530226* (2013.01); *A61F 2013/530489* (2013.01); *C08L 2203/12* (2013.01); *D10B 2509/026* (2013.01)

(58) Field of Classification Search
CPC ........... B01J 20/26; B01J 20/28; C08L 67/04; D01D 10/00; D01D 5/30; D01D 5/08; D01D 5/098; D01D 5/253; D01F 8/04; D01F 8/06; D01F 8/14; D04H 3/007; D04H 3/011; D04H 3/147; D04H 3/16; D04H 3/005; D04H 3/05; D04H 3/14; B32B 5/26
See application file for complete search history.

(56) References Cited

U.S. PATENT DOCUMENTS

| | | | |
|---|---|---|---|
| 7,780,903 B2 | 8/2010 | Topolkaraev et al. | |
| 7,850,899 B2 | 12/2010 | Kunze | |
| 2006/0134388 A1 | 6/2006 | Miller et al. | |
| 2011/0022014 A1 | 1/2011 | Suzuki et al. | |
| 2018/0051404 A1 | 2/2018 | Novarino et al. | |
| 2023/0218452 A1 * | 7/2023 | Kasparkova | B32B 5/022 604/368 |

FOREIGN PATENT DOCUMENTS

| | | |
|---|---|---|
| EP | 0 391 260 A1 | 10/1990 |
| EP | 2813611 A1 | 12/2014 |
| EP | 3 192 910 A1 | 7/2017 |
| IL | 283340 B2 | 11/2024 |
| JP | 2021529117 A | 10/2021 |
| MX | MX/a/2021/006019 | 9/2021 |
| RU | 2021117455 A | 12/2022 |
| TH | 2101002655 A | 7/2022 |
| WO | 2018059610 A1 | 4/2018 |

OTHER PUBLICATIONS

Nonwoven Fabrics: Raw Materials. Manufacture, Applications, Characteristics, Test Processes, edited by Wilhelm Albrecht, Hilmar Fuchs and Walter Kittelmann, published in 2003, Wiley-VCH.
Microfiber Nylon Spunbond: Production and Characterization, Vyas, Khyati B. published on May 31, 2006.
Textile Progress, vol. 44, No. 1, published in Mar. 2012.
Journal of Textile Engineering & Fashion Technology, vol. I, Issue Apr. 2017 published on Apr. 17, 2017.
EPO Communication pursuant to Rule 114(2) EPC issued in Application No. 19828196.6 dated Jun. 24, 2022.

* cited by examiner

| *after activation (oven, 120°C)* | |
|---|---|
| *Example 2F: PET/PP* | *Example 4: PET/PET* |
| *MD change: -15%*<br>*CD change: - 15 %*<br>*Thickness change: + 103%*<br>*Volume change: + 47%*<br>*Soft* | *MD change: - 63%*<br>*CD change: - 63 %*<br>*Thickness change: + 222%*<br>*Volume change: - 56%*<br>*Hard* |

| Before activation | After activation |
|---|---|

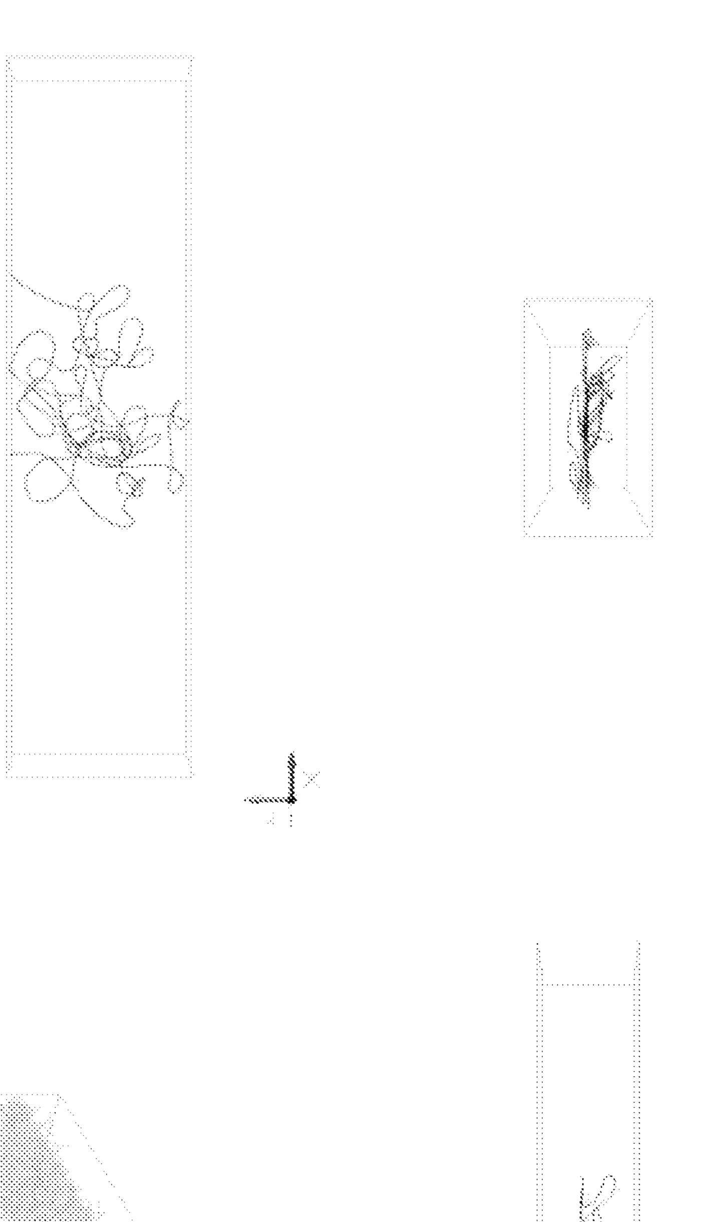
Fig. 6b

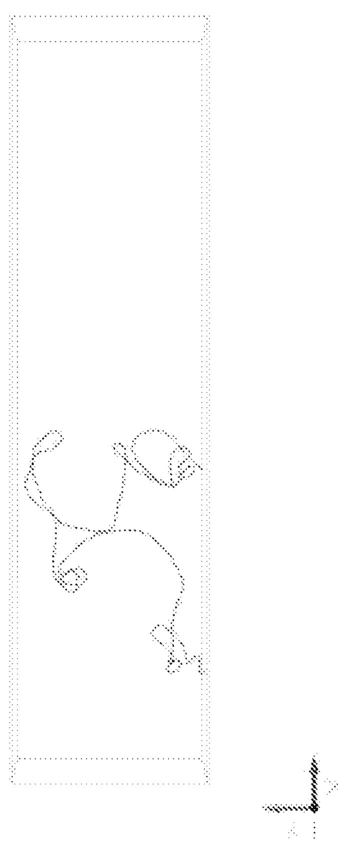
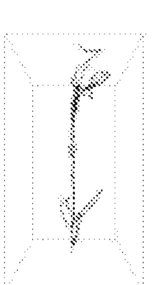
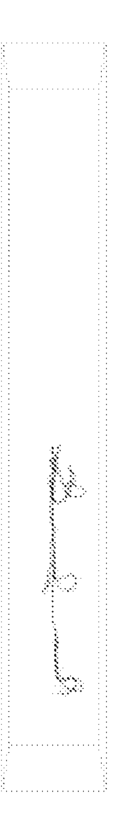
Fig. 6c

Micrographs of rayon fibers (7.8X); A = no crimp, B = medium crimp (5.8 crimps/cm), C = high crimp (7.6 crimps cm)

BULKY NONWOVEN FABRIC WITH ENHANCED COMPRESSIBILITY AND RECOVERY

CROSS-REFERENCE TO RELATED APPLICATIONS

This application is a U.S. national stage entry under 35 U.S.C. § 371 of PCT International Patent Application No. PCT/CZ2019/050053, filed Nov. 22, 2019, which claims priority to Czech Republic Patent Application No. 2018-647, filed Nov. 23, 2018, the contents of each of which are incorporated herein by reference in their entirety.

FIELD OF INVENTION

The invention relates to a bulky spunmelt-type nonwoven fabric with enhanced compressibility and recovery containing multicomponent fibers with a non-crimpable cross-section. More specifically, the invention relates to a nonwoven fabric comprising at least one layer, said layer comprising endless filaments,

- which comprise at least a first polymeric material and a second polymeric material having its melting point lower than the first polymeric material A,
- wherein the second polymeric material extends in the longitudinal direction of the filament and forms at least a part of the surface of the filament and
- the at least one layer of endless filaments comprises filament-to-filament bonds formed of the second polymeric material. The invention also relates to a method of producing such nonwoven fabric.

BACKGROUND OF THE INVENTION

A person skilled in the art will realise, for example, the advantages of multicomponent crimped or curled fibers with asymmetric (crimpable) cross-sections. It is well known in the industry, that certain combinations of polymers when arranged within a fiber in suitable arrangements, so called crimpable cross-sections, will provide fibers with crimping—even self-crimping immediately after spinning, or provide a certain level of latent crimping, that can be induced by activation, e.g. thermal activation. It is also well known that certain polymer composition combinations are better for softness and pliability and certain other polymer combinations are more suitable for good recovery. For example, the patent WO2018059610, filed on 3 Sep. 2016, describes the use of PET/PE compositions in an eccentric core/sheath arrangement to create a bulky layer providing a good combination of compressibility and recovery.

A person skilled in the art will also know that for certain applications, similar materials can also be produced using advanced carding technology. Carding is a well-known process consisting of several production steps, where the fibers are first produced, then they are cut into short (staple) fibers, possibly treated, arranged to form a fibrous layer and then bonded together. On the other hand, the spunmelt process is an online production process that forms the final nonwoven fabric from endless filaments in a single step. Carded materials are produced from staple fibers and the high number of ends of these fibers located lengthwise and crosswise in a nonwoven layer may be undesired for certain applications.

SUMMARY OF THE INVENTION

The objective of the present invention is to achieve a bulky nonwoven fabric that may be compressed with a rather low pressure and may also recover when the pressure is released.

The above mentioned and some other drawbacks of conventional art eliminated by the nonwoven fabric comprising at least one layer, said layer comprising endless filaments,

- which comprise at least a first polymeric material and a second polymeric material having its melting point lower than the first polymeric material,
- wherein the second polymeric material extends in the longitudinal direction of the filament and forms at least a part of the surface of the filament and
- the at least one layer of endless filaments comprises filament-to-filament bonds formed of the second polymeric material, wherein
- all components of the filaments are arranged across the cross-section of the filament in a non-crimpable configuration, and
- at least 20% of fibres has the length of the filament to the length of the fabric ratio higher than 1.2:1, and
- at least 10% of fibres has the length of the filament to the length of the fabric ratio higher than 1.5:1, and
- at least 10% of fibres has the length of the filament to the length of the fabric ratio lower than 2.5:1.

The drawbacks are also eliminated by a nonwoven fabric comprising at least one layer, said layer comprising endless filaments,

- which comprise at least a first polymeric material and a second polymeric material having its melting point lower than the first polymeric material,
- wherein the second polymeric material extends in the longitudinal direction of the filament and forms at least a part of the surface of the filament and
- the at least one layer of endless filaments comprises filament-to-filament bonds formed of the second polymeric material, wherein the nonwoven fabric has a structural softness of at least 80 ($m^4$ $mm^2$ $g^{-2}$), preferably at least 100 ($m^4$ $mm^2$ $g^{-2}$), preferably at least 110 ($m^4$ $mm^2$ $g^{-2}$) more preferably at least 120 ($m^4$ $mm^2$ $g^{-2}$) more preferably at least 130 ($m^4$ $mm^2$ $g^{-2}$) more preferably at least 140 ($m^4$ $mm^2$ $g^{-2}$), most preferably at least 150 ($m^4$ $mm^2$ $g^{-2}$) wherein $$\text{Structural softness} = \frac{\text{thickness}}{\text{basis weight}} \times \text{recovery} \times \frac{\text{compressibility}}{\text{basis weight}} \times 10^6$$

wherein

- thickness is the thickness of the nonwoven structure in mm,
- basis weight is the basis weight of the nonwoven structure in grams per square meter,
- recovery is the ratio (Tr)/(Ts), wherein (Ts) is the initial thickness of the nonwoven structure under pre-load of 0.5 kPa and (Tr) is the recovered thickness of the nonwovens structure measured after a 2.5 kPa load has been applied and afterwards released,
- compressibility is in mm the difference between the initial thickness of the nonwoven structure and the thickness of the nonwoven structure under 5 N load.

Preferably, the first polymeric material and/or the second polymeric material consists of or comprises as the majority component polymeric material selected from the group consisting of polyesters, polyolefins, polylactic acid, polyester copolymers, polylactide copolymers and blends thereof; and the first polymeric material is different from the second polymeric material.

Also preferably, the filaments have a core/sheath structure, wherein the first polymeric material forms the core and the second polymeric material forms the sheath.

The mass ratio of the first polymeric material to the second polymeric material is preferably 50:50 to 90:10.

The nonwoven fabric has preferably a basis weight of at least 5 gsm, preferably of at least 10 gsm, more preferably of at least 20 gsm, more preferably of at least 30 gsm, with advantage of at least 40 gsm and preferably not greater than 200 gsm, preferably not greater than 150 gsm, preferably not greater than 100 gsm, most preferably not greater than 80 gsm.

It is also advantageous, when the filaments have a median fibre diameter of at least 5 microns; preferably at least 10 microns; preferably at least 15 microns; most preferably at least 20 microns, and at most 50 microns; preferably at most 40 microns; most preferably at most 35 microns.

Preferably, the layer has a void volume of at least 65%; preferably of at least 75%; more preferably of at least 80%; more preferably of at least 84%; more preferably of at least 86%; more preferably of at least 88%; most preferably at least 90%.

The above drawback of conventional art are also eliminated by a method of producing a nonwoven fabric, the method comprising the steps a) melting and feeding at least a first polymeric material and a second polymeric material having its melting point lower than the first polymeric material to nozzles of a spinning beam, wherein the nozzles are configured to form endless filaments having all components arranged across the cross-section of the filaments in a non-crimpable configuration, wherein the second polymeric material extends in the longitudinal direction of the filament and forms at least a part of the surface of the filament, and the filament speed is within the range of 3000 and 5500 m/min,
b) cooling of the formed filaments by fluid medium having a temperature within the range of 10 to 90° C. and drawing the filaments with a draw down ratio within the range of 200-1300 to achieve a semi-stable crystalline state of at least the first polymeric material,
c) laying the filaments on a formation belt to form a nonwoven filamentary batt,
d) heating the nonwoven filamentary batt to a temperature within the range between 80 and 200° C. to activate shrinkage of the nonwoven filamentary batt, such that at least the polymeric material is transformed to a more stable crystalline state.

Preferably, the method further comprises the step of pre-consolidation of the nonwoven filamentary batt after step c) and before step d), wherein the pre-consolidation is made by heating the filaments to a temperature within the range of 80 to 180° C., preferably 90° C. to 150° C., most preferably 110° C. to 140° C. to partially soften the polymeric material to provide bonds of polymeric material between the mutually crossing filaments.

Preferably, in step b) the filaments are cooled and drawn within a first zone with a fluid medium having a temperature within the range of 10 to 90° C., preferably 15 to 80° C., most preferably 15 to 70° C., and then within a second zone with a fluid medium having a temperature within the range of 10 to 80° C., preferably 15 to 70° C., most preferably 15 to 45° C.

According to a preferred embodiment, the heating of the nonwoven filamentary batt in step d) is provided by exposing the batt to air having the temperature within the range of 80 to 200° C., preferably within the range of 100 to 160° C., for a period of 20 to 5000 ms, preferably 30 to 3000 ms and most preferably 50 to 1000 ms. The air is preferably driven through and/or along the batt having initial speed within the range 0.1 and 2.5 m/s, preferably within the range of 0.3 and 1.5 m/s.

The nonwoven filamentary batt is preferably heated in step d) such that it shrinks in the machine direction and cross direction by 20% or less, preferably by 15% or less, more preferably 13% or less, more preferably 11% or less, most preferably 9% or less, and increases its thickness by at least 20%, preferably by at least 40%, more preferably at least 60%, most preferably by at least 100%.

The nonwoven filamentary batt may be heated in step d) such that polymeric material softens to provide bonds of polymeric material between the mutually crossing filaments. Or, the nonwoven filamentary batt is heated after step d) such that polymeric material softens to provide bonds of polymeric material between the mutually crossing filaments. The heating after step d) to provide bonds of polymeric material (B) may be made using omega drum bonding device, or a flat belt bonding device or a multiple drum bonder, and/or by driving air through and/or along the nonwoven filamentary batt for a time period of 200 to 20000 ms, preferably in between 200 and 15000 ms and most preferably in between 200 and 10000 ms, wherein the air has the temperature within the range of 100° C. to 250° C., preferably 120° C. to 220° C. and initial velocity within the range of 0.2 and 4.0 m/s, preferably in between 0.4 and 1.8 m/s.

Preferably, the first polymeric material and/or the second polymeric material consists of or comprises as the majority component polymeric material selected from the group consisting of polyesters, polyolefins, polylactic acid, polyester copolymers, polylactide copolymers and blends thereof; and the first polymeric material is different from the second polymeric material.

When performing the method according to the invention, it is advantageous, when the draw down ratio is within the range of 300-800.

The above drawbacks of conventional art are also eliminated by an absorbent hygienic product comprising the above defined nonwoven fabric, wherein the nonwoven fabric forms at least one of a topsheet, an acquisition and distribution layer, an absorbent core, a backsheet and a landing zone for mechanical closures.

It is advantageous, when the topsheet and the acquisition and distribution layer are bonded together It is also advantageous, when the topsheet and the acquisition and distribution layer are a unitary material.

It is also advantageous, when the pores of this fabric are at least partially filled with particles of superabsorbent polymer It is also advantageous, when the backsheet and the landing zone are a unitary material.

Definitions

The term "acquisition/distribution layer" or "ADL" refers to a material layer typically in an absorbent hygiene product, typically a nonwoven, between the topsheet and the absorbent core. This layer is designed to quickly acquire and/or distribute a fluid away from the topsheet and into the core. This layer is sometimes called a "wicking layer", "surge layer", "acquisition layer" or "distribution layer". Articles having an ADL layer consisting of only one sub-layer (a bonded batt) are known. Articles having two sub-layers or more are also known. Ideally one sub-layer shall primarily pull the fluid quickly away from the topsheet and distribute the fluid in the direction towards the core and also in other directions throughout the layer. The other sub-layer/s should lower the tendency of fluid travel back from the core towards the first sublayer and towards the topsheet, i.e. to lower or prevent rewetting of the topsheet. These sub-layers typically do not comprise superabsorbent material. In the following, the term "acquisition-distribution layer" ("ADL") will be used to designate the layer present between the topsheet and the absorbent core providing these acquisition and distribution functions, irrespective of the number of fibrous sub-layers (batts) forming this layer.

The term "batt" refers to materials in the form of filaments that are found in the state prior to bonding, a process that can be performed in various ways, for example, air-through-bonding, calendaring etc. The "batt" consists of individual filaments between which a fixed mutual bond is usually not yet formed even though the filaments may be pre-bonded/pre-consolidated in certain ways, where this pre-consolidation may occur during or shortly after the laying of the filaments in the spunlaying process. This pre-consolidation, however, still permits a substantial number of the filaments to be freely moveable such that they can be repositioned. The above mentioned "batt" may consist of several strata created by the deposition of filaments from several spinning beams in the spunlaying process.

The term "filament" refers to a principally endless fiber, while the term "staple fiber" refers to a fiber which has been cut to a defined length.

The term "filament to filament bonds" refers to bonds which connect usually two filaments in an area, in which the filaments cross each other or locally meet or abut on each other. The bonds may connect more than two filaments or may connect two parts of the same filament.

The term "monocomponent filament" refers to a filament formed of a single polymer or polymer blend, as distinguished from a bicomponent or multicomponent filament. "Multicomponent fiber or filament" refers to a fiber or filament having a cross-section comprising more than one discrete section, where each of these sections comprises a different polymer component, or a different blend of polymer components, or polymer component and blend of polymer components. The term "multicomponent fiber/filament" includes, but is not limited to, "bicomponent fiber/filament." The different components of multicomponent fibers are arranged in substantially distinct regions across the cross-section of the fiber and extend continuously along the length of the fiber. A multicomponent fiber may have an overall cross-section divided into subsections of the differing components of any shape or arrangement, including, for example, coaxial subsections, core-and-sheath subsections, side-by-side subsections, radial subsections, islands-in-the-sea subsections, etc. A bicomponent filament having a "core/sheath structure" has a cross-section comprising two discrete sections each of which is comprised of a polymer or polymer blend, wherein the sheath polymer or polymer blend component is enclosed around the core polymer or polymer blend component.

"Fiber diameter" is expressed in units of μm. The terms "grams of fiber per 9000 m" (denier or den) or "grams of fiber per 10000 m" (dTex) are used to describe the fineness or coarseness of fibers, which are related to the diameter (when assumed to be circular) by the density of the employed material(s).

"Film"—means a skin-like or membrane-like layer of material formed of one or more polymers, which does not have a form consisting predominately of a web-like structure of consolidated polymer fibers and/or other fibers.

"Machine direction" (MD)—with respect to the production of a nonwoven web material and the nonwoven web material, machine direction (MD) refers to the direction along the web material substantially parallel to the direction of forward travel of the web material through the production line on which the web material is manufactured.

"Cross direction" (CD)—with respect to the production of a nonwoven web material and the nonwoven web material, cross direction (CD) refers to the direction along the web material substantially perpendicular to the direction of forward travel of the web material through the production line on which the web material is manufactured.

A "nonwoven" or "nonwoven fabric" or "nonwoven web" is a manufactured sheet or web of directionally or randomly oriented fibers which are first formed into a batt and then consolidated together by friction, cohesion, adhesion and bonded thermally (e.g. air-through-bonding, calender-bonding, ultrasonic bonding, etc.), chemically (e.g. using glue), mechanically (e.g. hydro-entanglement, etc.) or by combination thereof. The term does not include fabrics which are woven, knitted, or stitch-bonded with yarns or filaments. The fibers may be of natural or man-made origin and may be stapled or continuous filaments or be formed in-situ. Commercially available fibers have diameters ranging from less than about 0.001 mm to more than about 0.2 mm, and come in several different forms: short fibers (known as staple or chopped fibers), continuous single fibers (filaments or monofilaments), untwisted bundles of continuous filaments (tow), and twisted bundles of continuous filaments (yarn). Nonwoven fabrics can be formed by many processes including, but not limited to, meltblowing, spunbonding, spunmelting, solvent spinning, electro-spinning, carding, film fibrillation, melt-film fibrillation, airlaying, dry-laying, wetlaying with staple fibers, and combinations of these processes as known in the art. The basis weight of nonwoven fabrics is usually expressed in grams per square meter (gsm).

The term "absorbent hygiene product" herein refers to products or aids that absorb or retain bodily excretions; more specifically to products or aids, that are placed against the body or placed in the vicinity of the body of the user for the purpose of absorbing and retaining various bodily excretions. Absorbent hygiene products may include disposable diapers, diaper pants, underwear and pads intended for adults suffering from incontinence, female hygiene products, nursing pads, disposable changing pads, bibs, bandages and similar products. The term "excretions" refers to, in the sense used herein, namely to urine, blood, vaginal secretions, breast milk, sweat and feces.

As used herein, the term "layer" refers to a sub-component or element of a web. A "layer" may be in the form of a plurality of fibers made on a single beam or on two or more consecutive beams, which produce substantially the same fibers. For example, two consecutively arranged spunbond beams with substantially the same settings and polymer compositions can together produce a single layer. In contrast, for example, two spunbond beams, where one produces monocomponent fibers and the other bicomponent fibers, will form two distinct layers. The composition of a layer can be determined either by knowing the individual settings and components of the resin (polymer) composition used to form the layer, or by analyzing the nonwoven itself, using, for example, optical or SEM microscopy or by analyzing the composition used to make the fibers of the layer using DSC or NMR methods.

The "spunbond" process is a nonwoven manufacturing system involving the direct conversion of a polymer into continuous filaments, integrated with the conversion of the filaments into a random arrangement of laid filaments forming a nonwoven batt that is subsequently bonded to form a nonwoven fabric. Bonding process can be performed in various ways, for example, air-through-bonding, calendaring etc.

"Activation" herein refers to the process, whereby fibers or filaments or fiber structures being in a semistable state (for example not being crystallized in the lowest possible energy state) are heated and then slowly cooled so, that the semistable state changes to some other more stable state (for example a different crystallization phase).

The term "crimpable cross-section" herein refers to multicomponent fibers, where components with different shrinkage properties are arranged across the cross-section so, that when heated to or above the activation temperature and then slowly cooled down, the fibers crimp, which causes these fibers to follow the vectors of the shrinkage forces. Thereby, when the fiber is released, it creates a so-called helical crimp, although when contained within a fiber layer the mutual adhesion of the fibers does not permit the creation of ideal helixes. For a multicomponent fiber, we can determine the center of mass for each individual component in the fiber cross-section (considering their areas/positions in the cross-section). Not to be bound by a theory, we believe that when the centers of gravity of all areas of each of the components are substantially at the same point, the fiber is non-crimpable. For example, for a round bicomponent fiber with centric core/sheath structure the center of mass is in the center of the cross-section (see the FIG. 2).

The term "compressibility" herein refers to the distance in millimeters (mm) by which the nonwoven is compressed by a load defined by a "resilience" measurement.

The term "spinneret capillary density [1000/m]" herein refers to the number of capillaries placed on the spinneret per 1 m distance in the CD.

The term "filament speed" herein refers to a number calculated from the fiber diameter, the throughput and the polymer density of the filament.

The term "draw down ratio" herein refers to a number calculated by dividing the capillary cross-section area by the filament cross-section area. The measured fiber fineness based on its apparent diameter is used to calculate the filament cross-section area. Other non-round cross sections cannot be calculated in this way, thus in such cases the analysis of SEM images showing the actual cross-section is necessary.

The term "cooling air/polymer ratio" herein refers to a calculated number out of the cooling air mass flow divided by the polymer mass flow.

BRIEF DESCRIPTION OF THE DRAWINGS

Preferred embodiments of the invention will be further described in more detail with reference to the accompanying schematic drawings, which show

DETAILED DESCRIPTION OF EXEMPLARY EMBODIMENTS

The objective of the present invention is to achieve a bulky nonwoven fabric that may be compressed with a rather low pressure and may also recover when released. A person skilled in the art will realize the different ways for achieving such a material using crimped fibers. In contrast, we have found a surprising solution to the task of achieving this effect by means of endless fibers having a non-crimpable cross-section.

According to the invention, the nonwoven fabric comprises at least one layer formed mainly from endless filaments with a non-crimpable cross-section. The fibers can be multicomponent, preferably bicomponent. Not to be bound by a theory, we believe that when the center of gravity of surfaces formed by a component across the fiber cross-section is located in substantially the same location as the center of gravity of surfaces of each of the other components, the cross-section is non-crimpable.

Figure 1:
FIG. 1: Filaments shapes

For example, the layer according to the invention can comprise mainly endless filaments with a round cross-section, trilobal cross-section, star cross-section, etc. (FIG. 1). A person skilled in the art will realise many possible shapes of the fiber cross-section that will substantially neither crimp when cooled, nor involve latent crimping, which may, however, be activated by heating and subsequent cooling of the fibers.

Figure 2:
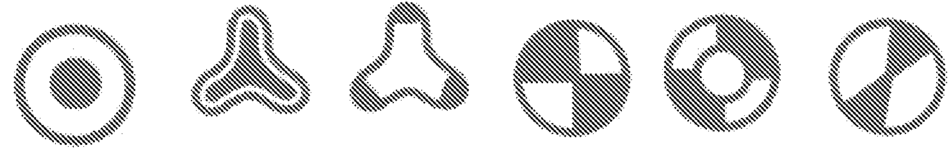
FIG. 2: Non-crimpable crossection

For example, endless filaments can be multicomponent filaments, where the component layout in the cross-section is core/sheath (concentric), segmented pie or any other layout with the centre of gravity of component areas in one location within the filament cross-section (FIG. 2).

Preferably, the layer according to the invention is formed from bicomponent core/sheath filaments with a round or trilobal shape.

According to the invention, the endless filaments are formed from two or more components, where one component brings a certain level of strength and rigidity that is necessary for the recovery feature and the other component brings softness and also is able to maintain a cohesive structure by forming bonds between the individual filaments. For example, the first component can be chosen from a group of polyesters (e.g. from aromatic polyesters such as polyethylene terephthalate (PET), or from aliphatic polyesters such as polylactic acid (PLA)), polyamides, polyurethanes or their copolymers or suitable blends. It is within the scope of the invention that the first component consists or consists essentially of a plastic of the group of polyesters that also includes polyester copolymers (coPET) or polylactide copolymers (COPLA). Preferably polyethylene terephthalate (PET) or polylactic acid (PLA) is used as the polyester.

For example, the second component can be chosen from a group of polyolefins (i.e. polypropylene or polyethylene), low-melting polymers, copolymers or blends of suitable polymers. It is within the scope of the invention that the second component consists or consists essentially of a plastic of the group of polyesters that also includes polyester copolymers (coPET) or polylactide copolymers (COPLA). Preferably polyethylene (PE) is used as the polyolefin.

The preferred combination of components for the bicomponent filaments in the nonwoven layer according to the invention are PET/PE, PET/PP, PET/CoPET, PLA/COPLA, PLA/PE and PLA/PP.

The preferred bicomponent filaments have the ratio of the mass of the first component to the mass of the second component from 50:50 to 90:10.

In another embodiment, the components can also contain additives to modify the filament properties. For example, the core can contain a color pigment or, for example, a nucleating agent. A person skilled in the art will understand that special combinations of nucleating agents can be found that can change the polymer crystallization and shrinkage behavior up to a significant level (as for example shown by Gajanan in U.S. Pat. No. 5,753,736, filed in 1995). On the other hand, for example, simple titanium dioxide, which is often used as a whitening coloring agent, will cause only an insignificant change in the polymer behavior that can be, in case of need, easily offset by a slight adjustment of the process conditions.

The sheath can contain, for example, a color pigment or a surface modifier (to attain, for example, a silky touch and feel quality). A person skilled in the art will realise many other options based on requirements of specific applications.

In another embodiment, the components can also contain a certain amount of different polymers. For example the first component (e.g. core) can contain a certain small amount of the second component (e.g. sheath) polymer or polymers, or vice versa the second component (e.g. sheath) can contain, for example, a small amount of first component (e.g. core) polymer or polymers. A certain content level can be used for exact polymer combinations. For example Moore teaches (US application US2012088424 from 3M innovative properties), that blend up to 10% of polypropylene to polyester will provide stable fibers.

Not to be bound by a theory, we believe that the key feature for the formation of the fabric with the desired properties is achieved by the combination of two components. Firstly, the component of the filament forming the nonwoven structure, according to the invention, forming, for example, the core, comprises of polymer A that is able to shrink under certain conditions. During the fiber formation process—especially during cooling and drawing—polymer A is designed to be able to undergo changes upon future activation. For example, polymer A is set to a semistable state (for example, not crystallized in the lowest possible energy state) and then during activation it is heated and then slowly cooled so that the semistable state changes to some other more stable state (for example different crystallization phase with a lower volume). This change results in inner shrinkage forces that we believe have their vector in the direction of the fiber center line.

Figure 3:
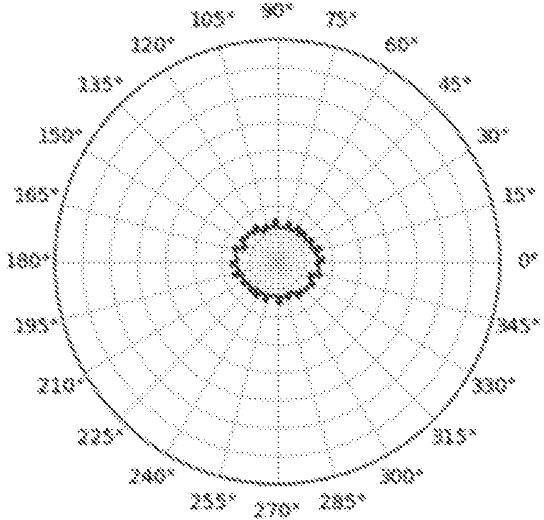
FIG. 3: Omnidirectionality of filaments in the layer according to exemplary embodiments of the invention

The fiber diameters within the spunmelt nonwoven are in the millimeter and/or submillimeter range; in general the fibers are omnidirectional (see FIG. 3) and contact each other so that the free parts between them are also generally in the millimeter and/or submillimeter range. The cohesion between the fibers acts against the inner force vector and forms the first resistance point against it. This resistance point can be also called threshold resistance point against structural shrinkage. For example, when one fiber is set to the proper state and undergoes activation, it can form, for example, irregular bows or waves in all 3 dimensions. In contrast, a fiber limited by the surrounding structure of its neighboring fibers does not have such freedom.

Figures 4, 5:
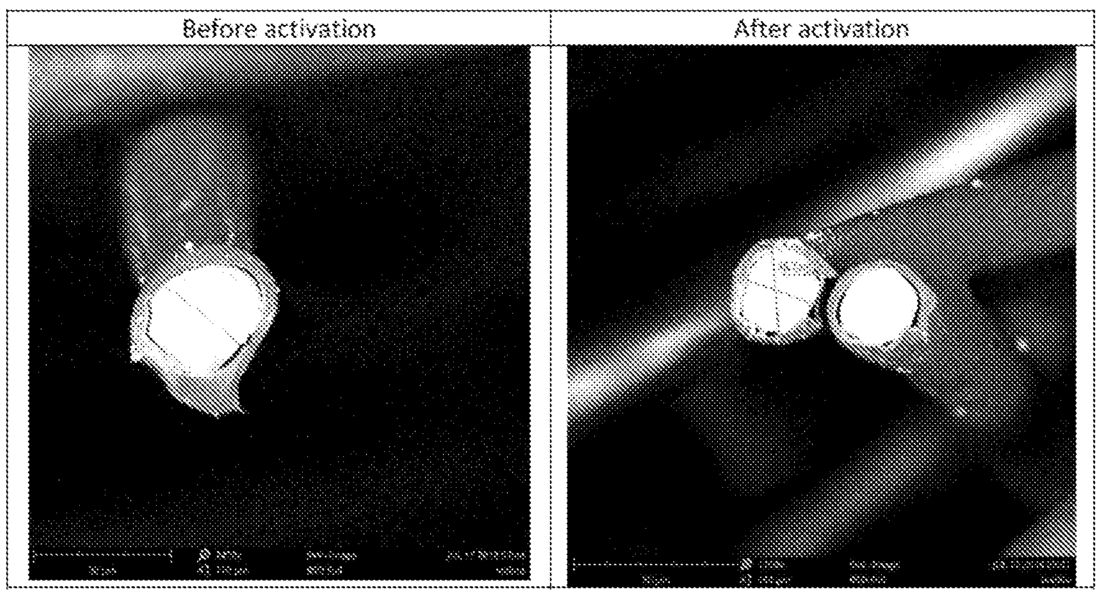
FIG. 4: Shrinkage of example 2F in contrast to shrinkage of example 4
FIG. 5: SEM microscopy photo of core/sheath fiber cross-section before and after activation FIG. 6 *a-c*: Examples of filament routes in the fabric according to the invention

The layer according to the invention is formed from bicomponent filaments, where the second component comprises of polymer B that has a lower melting point and preferably also provides other desired properties such as softness, pleasant touch and feel enhancing properties, etc. Polymeric material A and polymeric material B should differ in their shrinkage characteristics, preferably the polymeric material B (preferably the material forming the sheath of the filament) has a lower shrinkage potential than the polymeric material A (preferably forming the core of the filament). The result is differing shrinkage forces acting within the two adjacent polymeric materials. Not to be bound by a theory, we believe that the polymeric material A and the polymeric material B always have different characteristics, so that the vectors of the inner shrinkage forces are never the same at the same point in time. This inhomogeneity in forces forms the second threshold resistance point against shrinkage. This resistance point can also be defined as a threshold resistance point against fiber shrinkage. For example, by comparing the behavior of the layer formed from a monocomponent filament (e.g. PET) and a layer formed under the same conditions from bicomponent filaments (e.g PET/PP), we can find a significant difference. Both samples of the same size, produced under the same conditions, were exposed to the activation temperature of 120° C. for the same time. Mono PET shrunk to a small planar object, while, in contrast, the PET/PP structure increased its volume (small decrease in CD and MD plus a large increase in the z-direction—see Table 1 and FIG. 4).

TABLE 1

| after activation (oven, 120° C.) | |
|---|---|
| Example 2F: PET/PP | Example 4: PET/PET |
| MD change: −15%<br>CD change: −15%<br>Thickness change: +103%<br>Volume change: +47%<br>Soft | MD change: −63%<br>CD change: −63%<br>Thickness change: +222%<br>Volume change: −56%<br>Hard |

The batt layer according to the invention undergoing activation provides a CD or MD shrinkage of at most 20%, preferably of at most 15%, preferably maximum 13%, more preferably maximum 11%, more preferably maximum 9%.

The batt layer according to the invention undergoing activation provides a z-direction increase of at least 20%, preferably of at least 40%, preferably of at least 60%, preferably of at least 80%, more preferably of at least 100%.

With considerable simplification, we can say that a batt shrinkage level can be estimated by the single fiber shrinkage level.

The batt layer according to the invention undergoing activation provides a positive volume change; preferably the volume change is higher than 10%, preferably higher than 15%, more preferably higher than 20%.

A person skilled in the art will know that a sensitive process such as spunbonding can also be influenced by various other conditions that can also induce certain opposing forces acting against both fiber and structure shrinkage.

It is well known in the industry that certain combinations of polymers with different shrinkage levels arranged in a so-called crimpable cross-section provide for so-called crimping. This can be either immediate self-crimping or latent crimping, where the fibers have to be activated in order to exhibit crimps (for example, through thermal activation). Fibers with crimpable cross-sections provide regular crimps forming a so-called helical crimp. With considerable simplification, we can say that a fiber having a crimpable cross-section tends to bend in the direction towards the component with higher shrinkage, which causes a substantially uniform helical crimp. In other words, the crimpable cross-section causes the regular shifting of the inner force vectors of the first and second components towards each other. Not to be bound by the theory, we believe that the regularity of the shift is the main reason for the regularity of the crimp on the free single fiber. In contrast, according to our invention and not to be bound by a theory, on fibers that have a non-crimpable cross-section, we believe that the inner shrinkage force vectors of the first and second component do not provide any regular shift between each other, and thereby the fiber forms irregular bows or waves in arbitrary directions. With considerable simplification we can say that the fiber does not have a uniform tendency to bend towards a specific part of its cross-section or periphery, which results in its irregular final shape. After activation, the fiber cross-section remains substantially non-crimpable, see FIG. 5

Not to be bound by a theory, we believe that when the inner shrinkage force is weak and is unable to overcome the threshold fiber resistance point of the opposing forces, the fabric will remain unchanged. When the inner shrinkage forces are strong enough and able to overcome all the threshold MD/CD resistance points of the opposing forces, the fabric shrinks according to the MD/CD ratio and forms a flat structure. When the inner shrinkage force is just strong enough to overcome the threshold fiber shrinkage resistance points but not strong enough to overcome the threshold structural MD/CD shrinkage resistance points, the fibers will bend out like springs in various directions, facing the lowest structural resistance mainly from the z-direction, and will form the desired bulky structure. The desired inner fiber shrinkage force will be higher than the inner resistance point of the fiber, yet lower than the threshold structural MD-CD shrinkage resistance point.

Figure 6:
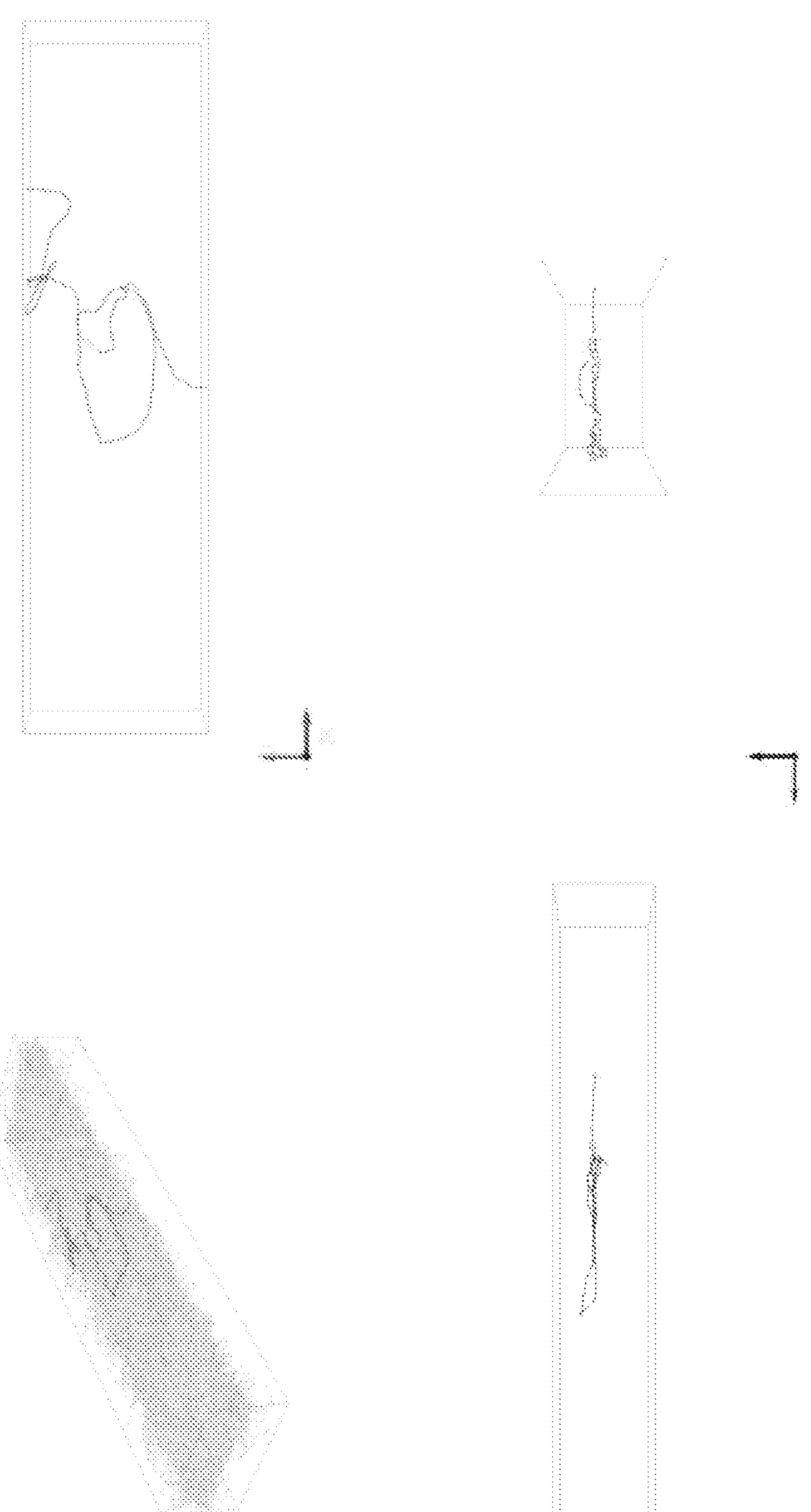

The layer, according to the invention, is formed from many fibers having many contacts between each other. Looking at it on the millimeter and/or submillimeter scale, we can find that the fibers, or better the millimeter and/or submillimeter parts of fibers are, due to their neighboring fibers, in a unique situation, where they face a unique combination of forces during activation, which results in a huge variety of filament shapes in the final structure. In contrast, the fiber can remain almost perfectly at the planar MD/CD level. On the other hand, the fiber can move "up" or "down" and form a large 3D structure in all MD, CD and z-directions. Some examples can be seen in FIG. 6. Not to be bound by theory, according to the invention, we believe that the variety of the filament routes in the layer brings an advantage in the final properties. According to the invention, at the macroscopic scale, the layer is homogenous. The variety of filament forms comprised within the layer and their mutual interactions presents the advantage of our invention, thus the layer is able to respond to external actions (e.g. pressure and release or fluid going through it) in the desired way.

With considerable simplification, we can also express the fiber route by means of the 'length of the filament to the length of the fabric' ratio.

The nonwoven fabric according to the invention contains:

at least 20% of fibers with a 'length of the filament to the length of the fabric' ratio greater than 1.2:1, preferably at least 30% of fibers with a 'length of the filament to the length of the fabric' ratio greater than 1.2:1, preferably at least 40% of fibers with a 'length of the filament to the length of the fabric' ratio greater than 1.2:1, more preferably at least 50% of fibers with a 'length of the filament to the length of the fabric' ratio greater than 1.2:1;

at least 10% of fibers with a 'length of the filament to the length of the fabric' ratio greater than 1.5:1, preferably at least 15% of fibers with a 'length of the filament to the length of the fabric' ratio greater than 1.5:1, preferably at least 20% of fibers with a 'length of the filament to the length of the fabric' ratio greater than 1.5:1, preferably at least 25% of fibers with a 'length of the filament to the length of the fabric' ratio greater than 1.5:1, more preferably at least 30% of fibers with a 'length of the filament to the length of the fabric' ratio greater than 1.5:1;

at least 5% of fibers with a 'length of the filament to the length of the fabric' ratio greater than 200%, preferably at least 10% of fibers with a 'length of the filament to the length of the fabric' ratio greater than 200%, preferably at least 15% of fibers with a 'length of the filament to the length of the fabric' ratio greater than 200%, more preferably at least 20% of fibers with a 'length of the filament to the length of the fabric' ratio greater than 200%;

The nonwoven fabric according to the invention contains:

at least 10% of fibers with a 'length of the filament to the length of the fabric' ratio less than 2.5:1, preferably at least 20% of fibers with a 'length of the filament to the length of the fabric' ratio less than 2.5:1, preferably at least 30% of fibers with a 'length of the filament to the length of the fabric' ratio less than 2.5:1, preferably at least 40% of fibers with a 'length of the filament to the length of the fabric' ratio less than 2.5:1, more preferably at least 50% of fibers with a 'length of the filament to the length of the fabric' ratio less than 2.5:1;

at least 5% of fibers with a 'length of the filament to the length of the fabric' ratio less than 200%, preferably at least 10% of fibers with a 'length of the filament to the length of the fabric' ratio less than 200%, preferably at least 15% of fibers with a 'length of the filament to the length of the fabric' ratio less than 200%, more preferably at least 20% of fibers with a 'length of the filament to the length of the fabric' ratio less than 200%.

Figure 7:
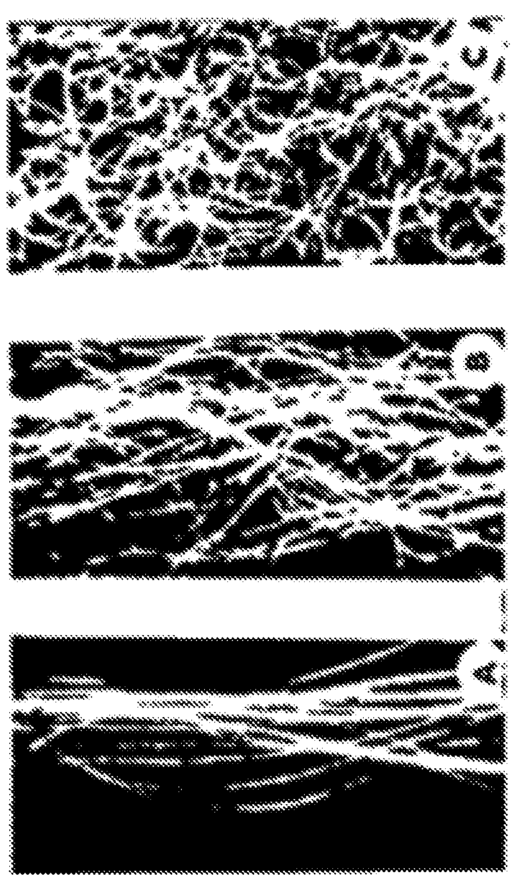
FIG. 7: Micrographs of fiber layers with different crimp level

In contrast to our invention, fibers with a crimpable cross-section tend to form regular shapes—helical crimps, wherein the fibers substantially tend to regularly bend towards that side of the fiber which comprises of the more shrinkable material. Although, they are also limited by their neighboring fibers; the regular force leads them to create substantial helixes. Not to be bound by theory, we believe that the greater the inner shrinkage force, the higher will be the 'crimps per length' unit on single fibers, and, therefore, there will be more helix parts found on the fabric structure. In contrast, when the crimping level is lower, for example, less than 25 crimps per inch (each single "round" on more than 1 mm of formed helix length), the free space between fiber contact points starts to be insufficient for the formation of a proper part of a helix, whilst the opposing forces caused by fiber contacts also become relatively stronger. It should be appreciated that set crimping numbers are just examples and can differ with various fiber compositions and/or process conditions. Below approximately 15 crimps per inch (each single "round" on more than 2 mm of formed helix length), the parts of helixes are hard to identify and below approximately 10 crimps per inch (each single round on more than approx. 2.5 mm helix length) the regular forces in the fiber are fully overcome by the opposing forces and contrary to the inner shrinkage vector shift and tend towards regular crimp formation, thus the structure may appear to be fully irregular. However, it should be appreciated that there may be different engines driving the bulky structure caused by the regular inner shrinkage vector shift (crimpable cross-section) and the bulky structure caused by irregular fiber shrinkage in the case of a non-crimpable fiber cross-section. Examples of structure differences based on a crimp of ryon fibers can be seen in FIG. 7 (discussed in article Fiber Crimp Distribution in Nonwoven Structure from Kunal Singha, Mrinal Singha from 2013 (available at http://article.sapub.org/10.5923.j.fs.20130301.03.html)

Figure 8:
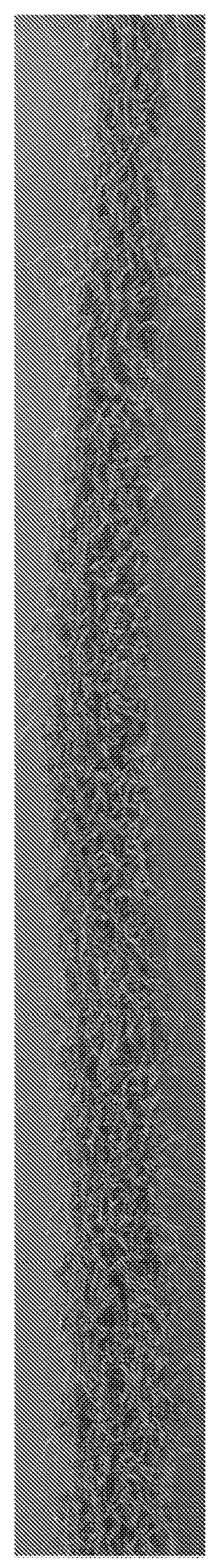
FIG. 8: Fabric cross-section—Example 7C (crimped fibers)

Although it is complicated to describe in a general way the structural differences distinguishing the nonwoven, according to the invention, and a nonwoven created from crimped fibers, especially in the case of lower crimp levels, a person skilled in the art can confidently determine the type of fabric they are inspecting. For example, there is a comparison of the SEM cross-section images of examples 7C (crimped) and 05A+D (according to the invention) in FIGS. 7-8.

In case of uncertainty, the component layout in the fiber cross-section becomes the most important factor. The layout may be known from production settings, or it can be estimated using "The type of fiber cross-section estimation" method.

The layer according to the invention combines several key properties, which need to be in proper balance. The layer itself shall be lofty and bulky, which can be described by layer thickness. The layer itself shall not be tough; it shall be pleasant and comfortable for the final user. For example, when used as an ADL in a hygiene absorbent product or as an example part of clothing, it shall provide a soft-loft. So when pressure is applied (for example, when sitting) it shall smoothly compress under low pressure. This can be described by compressibility in a length unit (e.g. mm). The layer itself shall also recover when freed from the pressure, i.e. what can be described by a recovery measurement. The balance of all the above-mentioned properties can be expressed by Structural softness.

$$\text{Structural softness} = \text{thickness}/\text{basis weight} * \text{recovery} * (\text{compressibility}/\text{basis weight}) * 10e6$$

$$\text{Structural softness} = \frac{\text{thickness}}{\text{basis weight}} \times \text{recovery} \times \frac{\text{compressibility}}{\text{basis weight}} \times 10^6$$

Where:

Thickness is in millimeters (mm)

Basis weight is in grams per square meter (gsm)

Recovery is a ratio without a unit

Compressibility in millimeters (mm)=compressibility (ratio without a unit)*thickness (mm) The layer according to the invention has a Structural softness of at least 40 $m^4$ $mm^2$ $g^{-2}$; preferably of at least 80 $m^4$ $mm^2$ $g^{-2}$; preferably of at least 100 $m^4$ $mm^2$ $g^{-2}$, preferably of at least 110 $m^4$ $mm^2$ $g^{-2}$, more preferably of at least 120 $m^4$ $mm^2$ $g^{-2}$, more preferably of at least 130 $m^4$ $mm^2$ $g^{-2}$, more preferably of at least 140 $m^4$ $mm^2$ $g^{-2}$, with advantage of at least 150 $m^4$ $mm^2$ $g^{-2}$ The layer according to the invention has a basis weight of at least 5 gsm, preferably of at least 10 gsm, more preferably of at least 20 gsm, more preferably of at least 30 gsm, with advantage of at least 40 gsm. The layer according to the invention has the basis weight not greater than 200 gsm, preferably not greater than 150 gsm, preferably not greater than 100 gsm, most preferably not greater than 80 gsm.

The layer according to the invention has a thickness relative to basis weight (thickness recalculated to 1 gsm=thickness (mm)/basis weight (gsm)) of at least 5e10-3, preferably of at least 10e10-3, more preferably of at least 12e10-3.

The layer according to the invention has a recovery of at least 0.8 (which corresponds to 80% recovery of the original thickness), preferably of at least 0.82, more preferably of at least 0.84, most preferably of at least 0.85.

The layer according to the invention has the compressibility for each 1 gsm of layer basis weight of at least 0.25 microns (0.00025 mm), preferably of at least 0.75 microns (0.00075 mm), preferably of at least 1.25 microns (0.00125 mm), more preferably of at least 1.75 microns (0.00175 mm). So, for example, a 100 gsm layer has the compressibility of at least 25 microns (0.025 mm), preferably at least 75 microns (0.075 mm), preferably at least 125 microns (0.125 mm), more preferably at least 175 microns (0.175 mm).

The layer according to the invention has a resilience of at least 5%, preferably of at least 8%, more preferably of at least 10%, more preferably of at least 13%, more preferably of at least 15%.

The layer according to the invention comprises, most preferably of filaments with a median fiber diameter of at least 5 microns; preferably of at least 10 microns; preferably of at least 15 microns; with advantage preferably of at least 20 microns. In exemplary embodiments, the layer according to the invention consist of filaments with median fiber diameter of no more than 50 microns; preferably of no more than 40 microns; with advantage preferably of no more than 35 microns.

The thickness of fibers and also the distribution of fiber thicknesses can affect many other parameters. For example, for certain applications, the homogenous fiber thickness distribution can be taken advantage of, i.e. where the fibers are substantially the same, the vector forces in them are substantially comparable and the final fabric is substantially homogenous. Such a material can be advantageous, for example, for hygiene applications. For example, for certain other applications, a wide fiber thickness distribution can be taken advantage of, i.e. where there are thicker and thinner samples within the fabric. Not to be bound by theory, we believe that from a certain level, the vector forces in thick fibers are much stronger than the vector forces in thin fibers and thus thick fibers can become the dominant activator and form the final state of the nonwoven fabric, whereas the vector force in thin fibers can be suppressed. The final structure, where thick fibers form something like an inner skeleton, can be advantageous, for example, for filtration. The combination of thick and thin fibers can be produced using mixed filaments (mixed spunbond described for example at application WO2009145105 from Mitsui) or can be produced using consecutive beams, under the condition that the batt from each beam remains open enough to enable the thick and thin fibers to merge into a single structure.

In another embodiment of this invention, the layer is defined by its void volume, which is defined as the volumetric percentage of the total volume of void spaces in a material with respect to the bulk volume occupied by the material. A person skilled in the art will know that the void volume can be measured by many different methods. For the purposes of this document, the discussed void volume is calculated from the known basis weight (gsm), average polymer density and known bulk volume (fabric thickness or caliper of 1 square meter).

According to the invention, the layer has the void volume of at least 65%; preferable of at least 75%; more preferably of at least 80%; more preferably of at least 84%; more preferably of at least 86%; more preferably of at least 88%; with advantage of at least 90%.

Figure 10:
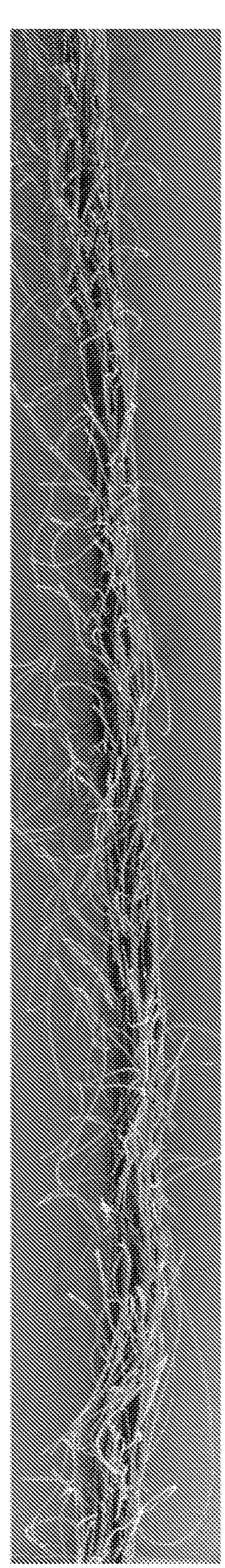
FIG. 10: Fabric cross-section—fabric according to an exemplary embodiment of the invention
Figure 11A:
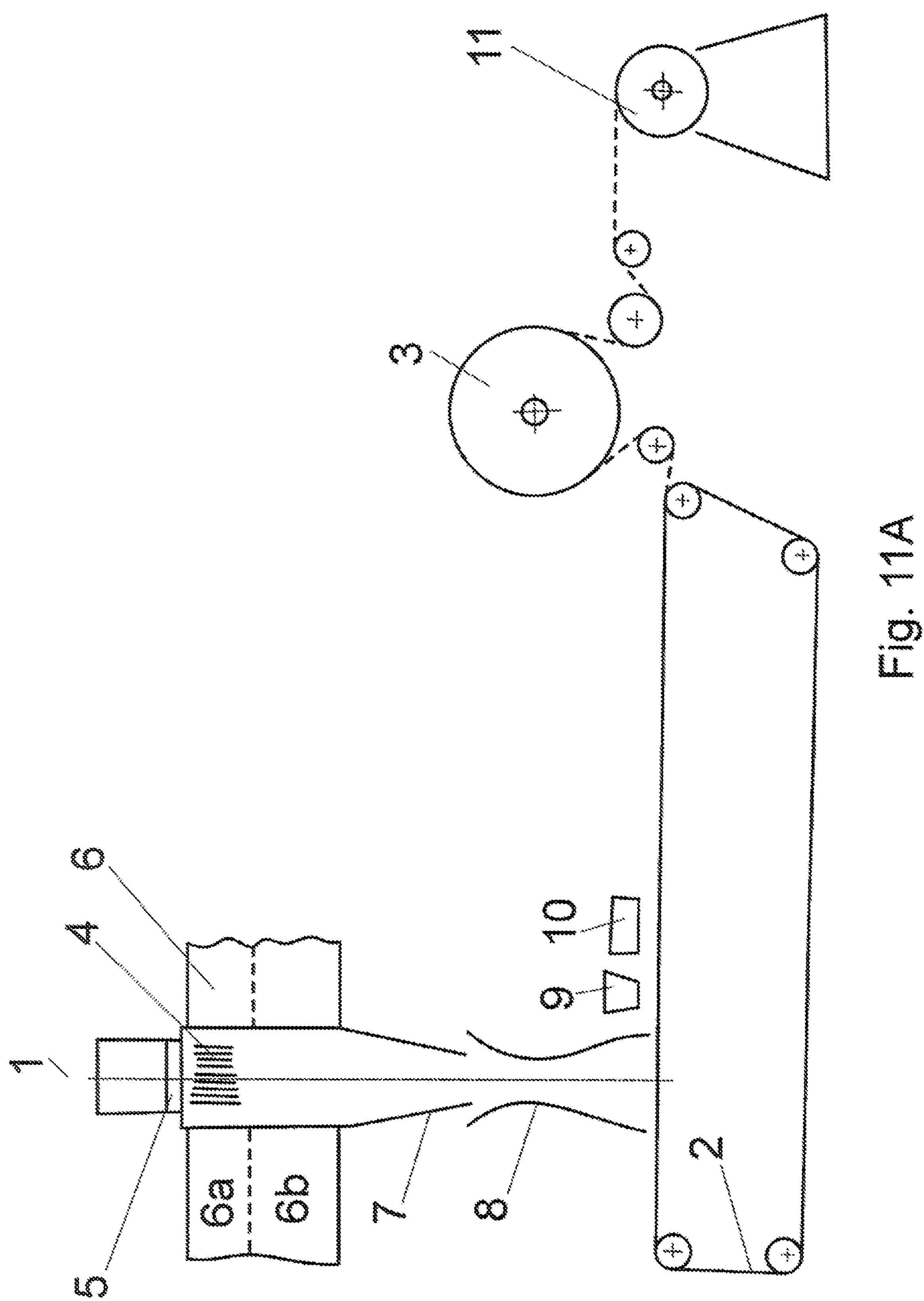
FIGS. 11A and 11B: Production lines suitable for performing the method according to an exemplary embodiment of the invention
Figure 11B:
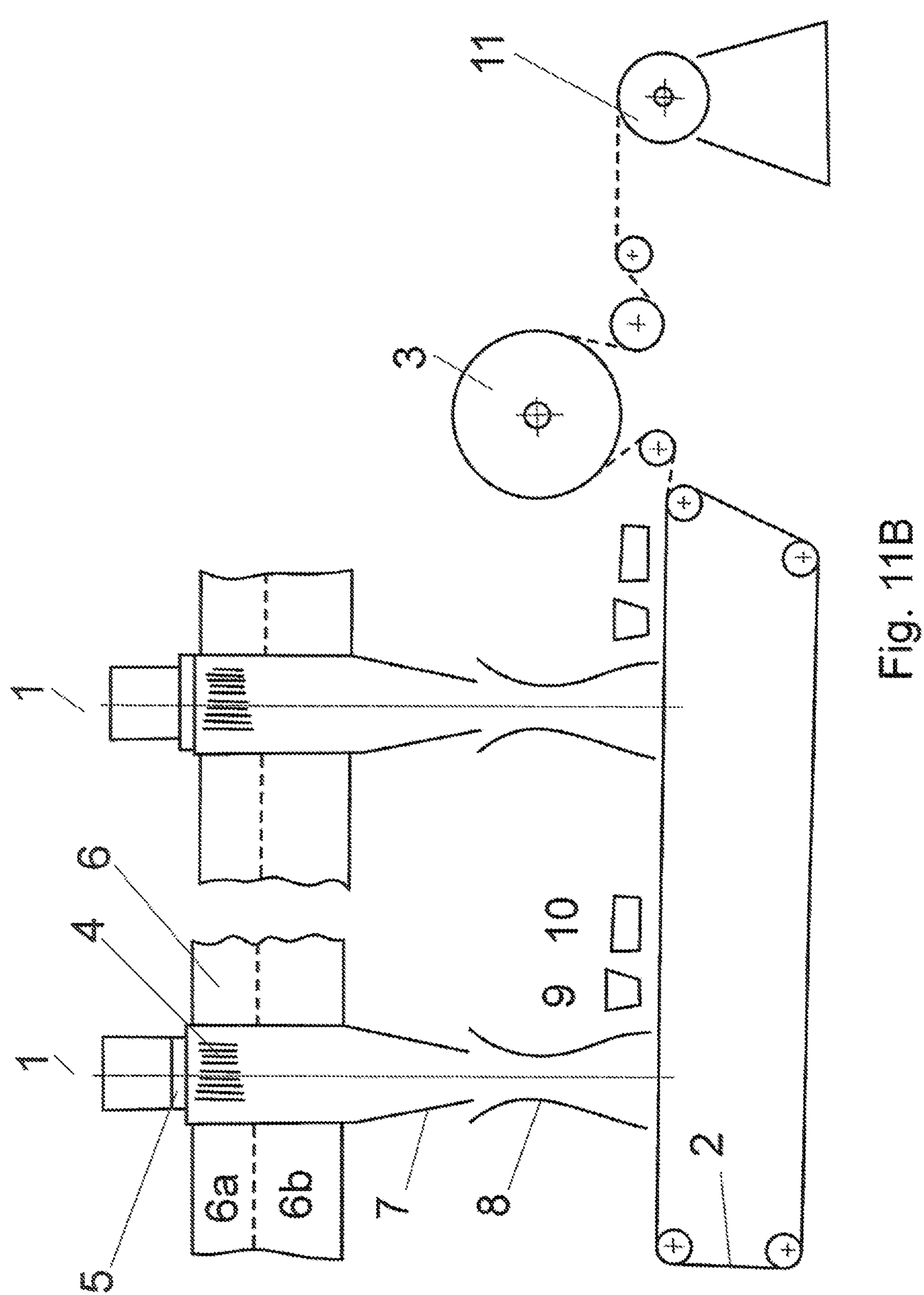
Figure 12A:
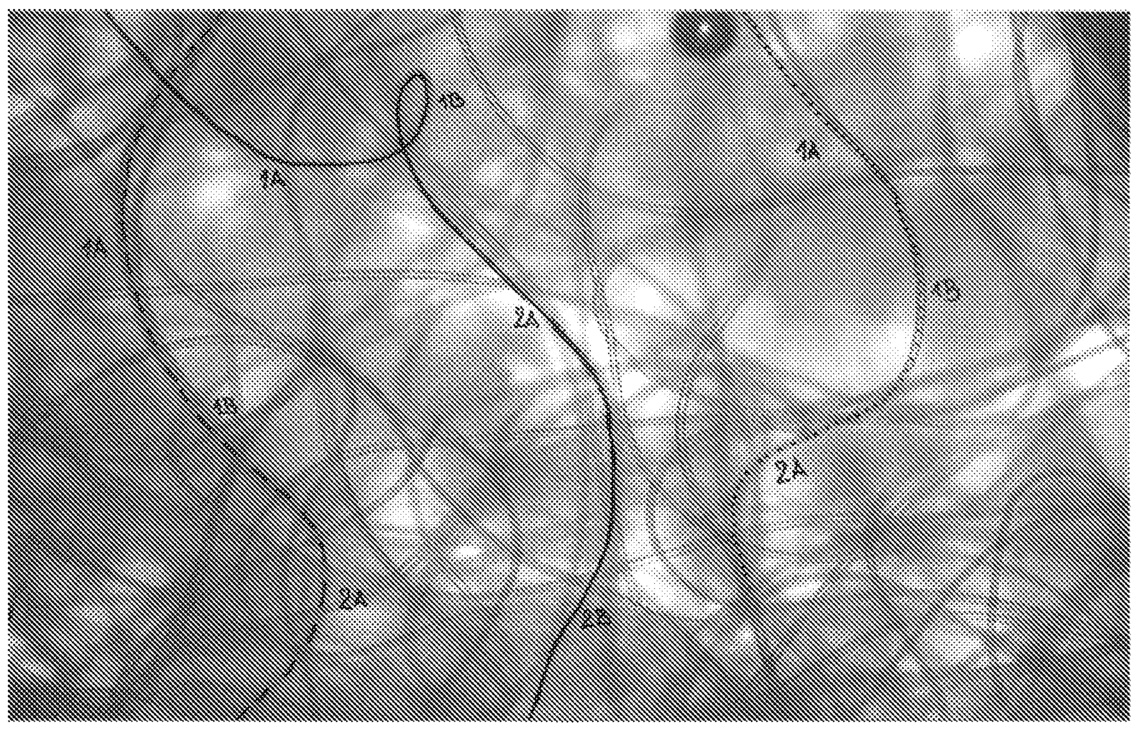
FIG. 12: "length of the filament to the length of the fabric ratio"—illustrative image to b)
Figure 12B:
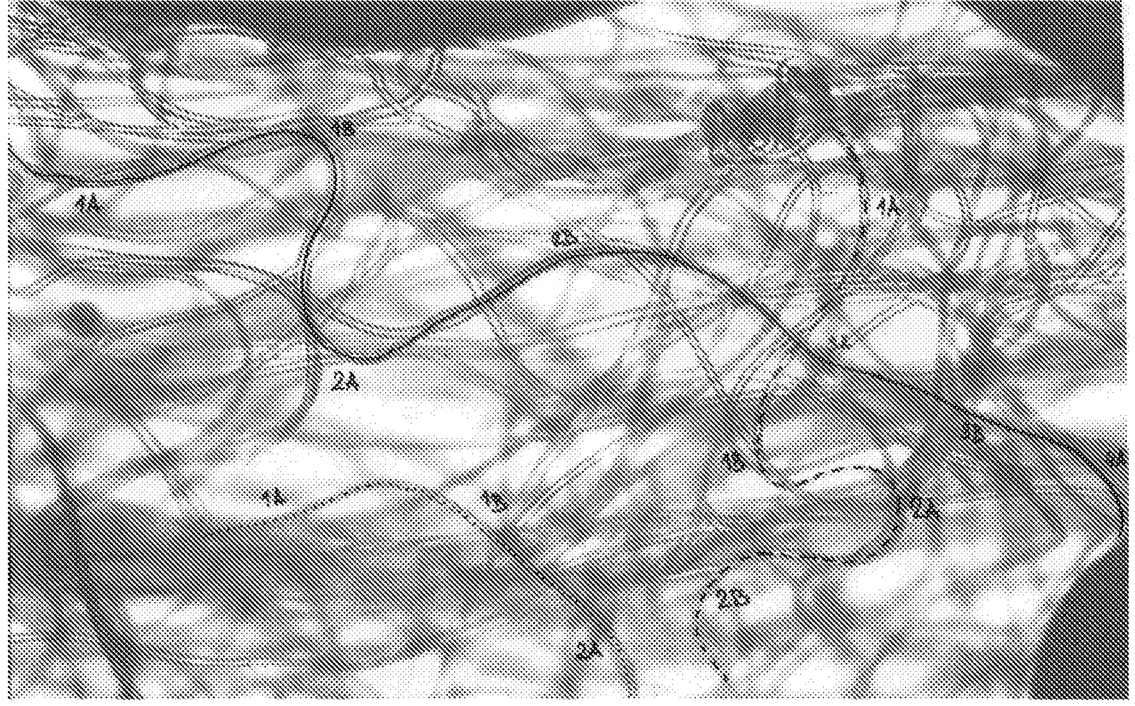
Figure 12C:

In another embodiment of this invention, a lofty voluminous nonwoven structure is provided with a multiplicity of singular filament loops and/or loop bundles protruding from the surface to the outside, as illustrated on the microscope image (FIG. 10). Not to be bound by theory, we believe that these "hairs" on the surface have at least two functions:

a. For example, in an application such as an acquisition distribution layer, these hairs help to interconnect the lofty ADL structure with the topsheet on the one side and on its other side with the absorbent core below the ADL. This interconnection of fibrous structures of the layers in an absorbent product improves the fluid transfer through the layers into the absorbent core.

b. For example, in an application requiring direct contact with the user's skin, these hairs improve the tactile softness and make the fabric more pleasant to touch and/or wear. For example, in hygiene applications, the advantage can be appreciated on soft-loft topsheets and/or backsheets. For example, on the protective garments it can be used on the side facing the user's skin.

Single use absorbent hygiene products like diapers, pant-type diapers or pads consist of many fibrous elements which can be made of nonwoven materials. Examples of such nonwoven elements are topsheets, backsheets, standing up leg gathers, landing zones for mechanical "hook and loop" closures etc. In some absorbent hygiene products, a previously typical absorbent core made of a mixture from cellulosic fluff pulp and superabsorbent polymers has been replaced by nonwoven layers containing superabsorbent polymer particles bonded to or between these layers by different means like glue, ultrasonic welding, thermal welding etc.

The bulky nonwoven fabrics/structures according to this invention can be produced in a wide range of basis weights. The lighter nonwovens in the range of 5-35 gsm show ideal properties for outer layers of absorbent hygiene products, e.g. topsheet and backsheet, as they are very soft, flexible, resilient which are the mechanical requirements for materials staying in contact with human skin.

The high bulkiness and open surface structure of nonwoven fabric according to this invention offer a perfect "looped" surface as a "landing zone" for "hooks" on the closure means of mechanical fasteners. The material according to this invention can be used as the landing zone on top of a backsheet but also form a part of backsheet's surface. In the latter case the backsheet and the landing zone will form a unitary material fulfilling both functions: Backsheet and landing Zone. The nonwoven landing zone in the absorbent article is described for example in patent application US2018318153 filled by Procter and Gamble company.

Nonwoven fabrics according to this invention produced in higher basis weights like 36-120 gsm offer superior properties as Acquisition and Distribution Layers in absorbent hygienic products. The outstanding shape memory resulting in advantageous resilience and recovery of the structure allow to improve the fluid (e.g. urine) flow management in absorbent products, especially in cases of multiple wetting as in the night situation. Use of Acquisition Distribution Layer in an absorbent article is described for example in patent application US2018296402 filled by Procter and Gamble company.

A combination of a topsheet and the ADL, both made according to this invention, will result in a unitary material forming the contact surface to the skin of the wearer and the surge management element below the topsheet. These two layers in that unitary material can be separately produced and bonded together or can be produced as a multi-layered material in one process. Unitary topsheet and absorbent article is described for example in patent application US2018311082 filled by Procter and Gamble company.

The open structure of nonwoven materials according to this invention results in a very high void volume. These void spaces in the fibrous structure called pores can be used as containers for particles of superabsorbent polymers. A person skilled in the art will know how to introduce the particles into the fibrous structure, e.g. by applying vibration.

The invention relates to a method for producing a nonwoven fabric from continuous filaments, in particular from continuous filaments of thermoplastic material. In the context of the invention nonwoven fabric layers made up of or consisting of continuous filaments are used. It is known that due to their quasi-endless lengths, continuous filaments differ substantially from staple fibers, which have much shorter lengths, for example 10 mm to 60 mm.

A recommended embodiment of the invention is characterized by at least one nonwoven layer being formed as a spunbonded nonwoven fabric by means of a spunbond process. The nonwoven fabric can be formed from several layers. This embodiment of the invention has been particularly successful. The multicomponent or bicomponent filaments of the nonwoven fabric layer are spun by a spinning device or spinneret and then passed preferably for cooling through a cooling device. In the cooling device, the filaments are conveniently cooled using a fluid medium, in particular by means of cooling air. It is within the scope of the invention that the spun filaments are then passed through a drawing device, and the filaments are drawn. The drawn filaments are then deposited on a tray—preferably laid on a formation moving belt to form a nonwoven batt. In particular, by adjusting the parameters which are controlling the draw down ratio, filaments with a controlled shrink potential can be created within the nonwoven layer. According to a preferred embodiment of this invention, a diffuser interposed as a storage device managing the laying down of the filaments is installed between the drawing device and the deposition location. It is within the scope of the invention that at least one diffuser, having divergent opposite side walls in relation to the flow direction of the filaments is utilized. A particularly recommended embodiment of the invention is characterized in the drive unit of the cooling device and the drawing device being designed as a closed system. In this closed system, in addition to the supply of the cooling medium or cooling air into the cooling device, no further air supply from outside is utilized. Such a closed system has proven itself superior in the production of nonwovens.

It has been found that technical problem according to the invention with the inventive shrinkage is particularly reliable in operation and effectively released when the closed unit described is used and when it is at least used in addition to a particularly preferred embodiment, a diffuser between the drawing device and storage. It has already been indicated that the shrinkage potential of the nonwoven sheet, produced by means of the spunbond method, can be adjusted or controlled very specifically by the parameters draw down ratio, cooling air/polymer ratio and filament speed.

As already defined, the spunbond production method is the direct conversion of polymers into continuous filaments, which are subsequently laid in a deposition location in a random fashion to create a nonwoven layer comprised of these filaments. The spunbond process defines both the properties of a single filament as well as the properties of the final nonwoven fabric. It is not always possible to use the finished nonwoven fabric to determine the various properties and states of individual filaments, such as rheological properties, polymer structural properties and shrinkage potential, present during the individual nonwoven production process steps. In general, the shrinkage potential of a nonwoven layer determines its ability to generate a bulky nonwoven by utilizing the shrinkage of single filaments into an increased relative thickness of the filament batt, however, without disintegrating the fabric structure and/or changing the length and the width of the filament batt significantly.

It is within the scope of the invention that the capacity for fibers to shrink is defined by utilizing different raw materials in the composition of continuous filaments and/or by setting different process conditions in the production of the continuous filaments of the nonwoven fabric and/or by utilizing different filament cross-section shapes in continuous filaments and/or adjusting the mass ratio between the different input materials and/or by arranging different orientations of the continuous filaments.

A particularly recommended embodiment of the method according to the invention is characterized by a nonwoven fabric that is produced from multicomponent filaments, in particular bicomponent filaments, having substantially non crimpable cross-sections, in a core-sheath configuration or other bicomponent fibers with a substantially noncrimpable configuration (FIG. 2). The multicomponent or bicomponent configuration should not be able to generate internal forces within the filament which can initiate regular crimping or curling of the filament.

The first component of the filament, forming, for example, the core, is comprised of polymeric material A that is able to shrink under certain conditions. The second component of the filament, forming, for example, the sheath, is comprised of polymeric material B, which differs from polymeric material A. For example, it contains a different polymer or blend of polymers. Advantageously, the difference between the melting temperature of polymeric material A and the melting temperature of polymeric material B, according to a preferred embodiment of the invention, is greater than 5° C., preferably greater than 10° C. The first component can be chosen from a group of polyesters (e.g. from aromatic polyesters such as polyethylene terephthalate (PET), or from aliphatic polyesters such as polylactic acid (PLA)), polyamides, polyurethanes or their copolymers or suitable blends. It is within the scope of the invention that the first component consists or consists essentially of a plastic of the group of polyesters that also includes polyester copolymers (coPET) or polylactide copolymers (COPLA). Preferably polyethylene terephthalate (PET) or polylactic acid (PLA) is used as the polyester.

The second component can be chosen from a group of polyolefins (i.e. polypropylene or polyethylene), low-melting polymers, copolymers or blends of suitable polymers. It is within the scope of the invention that the second component consists or consists essentially of a plastic of the group of polyesters that also includes polyester copolymers (coPET) or polylactide copolymers (COPLA). Preferably polyethylene (PE) is used as the polyolefin. The preferred combination of components for the bicomponent filaments in the nonwoven layer according to the invention are PET/PE, PET/PP, PET/CoPET, PLA/COPLA, PLA/PE and PLA/PP.

The preferred bicomponent filaments have the ratio of the mass of the first component to the mass of the second component from 50:50 to 90:10. It is in the context of the process according to the invention that the mass ratios of the core-sheath configuration can be freely varied during production without stopping the machine.

Process advantages are provided by filaments with non-crimpable cross-sections over crimping filaments in achieving bulky and soft-loft materials. Unlike non-crimpable fibers, filaments that exhibit (self)crimping during production are not easy to control. Most of the crimpable cross-section filament types develop crimps during the laydown process and/or with activation. Since they move relative to each other during the crimping process, they can easily touch each other or entangle, in different words they can hinder each other. Thus, nonwoven layers consisting of self-crimping filaments are often limited in their design due to the uneven fiber distribution caused by the relative movement of the filaments. The resulting necessary work-arounds often include reduced throughput, slower production speeds and special intermediate process steps for fixing the filaments to each other.

This invention does not utilize self-crimping filaments and thus a far more uniform laydown can be achieved, which enables a lower possible basis weight while retaining requested fabric properties and/or higher production line speeds with higher throughputs. With non-crimping filaments, the production process is much easier to control and the production of spinning nozzles/spinning beams is cheaper.

It is within the scope of the invention that the resulting nonwoven layer is thermally pre-bonded, i.e. pre-consolidated, thermally activated and thermally bonded. Thermal activation and bonding are preferably carried out with the aid of at least one hot fluid and/or by contact with a hot surface. The hot surface may be part of a roller, in particular. It is desired that thermal activation is performed under the condition that the shrinkage occurs uniformly over the entire surface of the fibrous layer. Thermal activation can be performed in a hot-air box or the batt can be passed through an oven. Thermal activation and bonding can also be performed by means of UV light, carried microwave and/or laser irradiation. It should be emphasized that thermal bonding in the context of the present “inline” process can also be carried out immediately following the completion of upstream process steps or both the process steps of thermal activation and bonding may be “offline”, thus decoupled from the upstream process steps. Thermal activation can, therefore, in principle, be performed “offline” at another time and in another place. Thus, a nonwoven that is not yet thermally activated and still not very bulky can be transported in a simple and space-saving manner to another processing location.

The desired level of pre-consolidation of the web/batt is highly dependent on the production process conditions. The key is to correctly set the level of fiber-to-fiber cohesion within the batt and, thereby, control the level of batt coherence based on the requirements of the subsequent production step. In the case of an online production process with activation on the belt itself, the desired level of cohesion is rather low, and required only for preventing tears or thinning caused by significant undesirable fiber movements during the activation process. In special cases, for example when the fibers themselves provide very good cohesion in contact with each other or their underlay, caused, for example, by their cross-section shape, entanglement rate or material composition, the cohesion of the batt may be good enough even without thermal pre-consolidation. In other cases, for example when the production process is divided into two steps and when prior to full activation the pre-consolidated batt is transported for example in the form of rolls, the required level of cohesion is much higher and so the pre-consolidation level also needs to be far higher. Persons skilled in the art having knowledge of their process conditions will easily recognize the level of pre-consolidation required for their specific case.

The activation temperature is preferably in the interval range between glass transition temperature and softening temperature (vicat softening temperature ISO DEN 306) of component/s A, preferably the core component. It should be appreciated that the optimal activation temperature can be chosen for the given composition of the component.

The invention provides bulky nonwoven fabrics formed using filaments with adjusted or controlled shrinkage potential of the nonwoven filaments. The shrinkage occurs uniformly over the entire batt, thus the process should provide uniform nonwoven properties ensuring uniform controlled shrinkage.

In the cooling device, the filaments are conveniently cooled by a fluid medium, in particular by cooling air. As already mentioned the potential shrinkage of the filaments needs to be uniformly distributed across the full length, width and thickness of the final nonwoven. Shrinkage characteristics can be modified by adjusting draw down ratio, cooling air/polymer ratio and filament speed, thus the invention includes that these parameters are almost uniform for each individual filament.

It is within the invention that the formed nonwoven fabric consists of several layers, each formed on a spunbond beam (1). It is understood that multiple layers are laid on top of each other and transported together on at least one forming belt (2) to a final bonding device (3). The filaments (4) are spun from a spinneret (5). The arrangement of the filaments is optimized by a staggered arrangement so that each filament gets a very similar mass and a very similar temperature of cooling air. The spinnerets can vary in number of capillaries as well in the diameter (d) and the length (I) of the capillaries. The length (I) is typically calculated as multiple of the capillary diameter and for this application is in the range from 2 to 10 l/d. The number of capillaries must be chosen based on the required final filament diameter and the required or planned total polymer throughput together with the required filament spinning speed. The number of capillaries can be varied from 800-7000 capillaries per meter, providing a filament diameter range from 8 to 45 μm. The capillary diameter and the filament speed are chosen in order to be able to generate the right level of shrinkage potential in the final filament. Filament speed should be defined between 3000 and 5500 m/min, the capillary diameter should be in between 200 and 1000 μm, resulting in a draw down ratio suitable for the process from 200 to 1300 in case of round capillaries, to reach the desired level of line productivity, more suitable for the process is a draw down ratio from 300 to 800 in case of round capillaries. Non-round capillaries show typically higher draw down ratios, greatly dependent on the capillary shape and its surface-to-volume ratio. The volume and temperature of the cooling air is set to achieve the correct draw down ratio and cooling conditions. Helpful for this invention, a cooling air/polymer ratio of 20 to 45 has been identified. The volume and temperature of the cooling air is controlled in the cooling device (6). The temperature can be set between 10° C. and 90° C., preferably the temperature can be set between 15° C. and 80° C. so that the shrinkage can be controlled by the cooling conditions. The cooling conditions define how fast the filaments cool down from melt temperature at spinning to glass transition temperature. For example, a higher cooling air temperature results in a delayed cooling of the filaments. As per the invention, in order to achieve the required and useful temperature range for the cooling air, in practice it is easier to handle temperature ranges when the cooling device is divided into 2 different zones in which the temperature can be controlled separately. In the first zone (6*a*), which is near to the spinneret, the temperature can be set between 10° C. and 90° C., preferably the temperature can be set between 15° C. and 80° C. and most preferably between 15° C. and 70° C. In the second zone (6*b*), which is close to the first zone, the temperature can be set between 10° C. and 80° C., preferably the temperature can be set between 15° C. and 70° C. and most preferably between 15° C. and 45° C.

Thereafter, the filaments are guided through the draw down zone (7). The filaments are drawn down by pulling forces created by the air speed of the cooling air. The volume of cooling air and the adjustable geometry of the draw down zone results in an air speed, which is also converted into filament speed. The filament speed together with the polymer throughput also defines the filament diameter. Potential shrinkage is controlled by the filament speed, the draw down ratio and the cooling air/polymer ratio.

In the next step, the filaments are guided to the diffuser (8) which has divergent side walls in relation to the flow direction of the filaments. These walls can be adjusted and are adjusted in a way to achieve a uniform nonwoven fabric in which single filaments create a filament laydown arrangement exhibiting omnidirectional orientation in the MD/CD plane.

It is understood that a filament laydown is influenced by the air guiding the filaments in the diffuser. The air can be adjusted to create arrangements from distinct zigzag lay down arrangements to real round loops, and furthermore CD-orientated elliptical structures. The filaments are laid down on the formation belt and transported into at least one pre-consolidation device (9). Cooling air is moved through the filament lay down layer and the formation belt out of the process. The volume of suction air can be adjusted to help the filament lay down and also to ensure that the filament batt is fixed on the formation belt. The pre-consolidation device is located close to the diffuser. The filament batt is controlled on the way from the diffuser to the pre-consolidation device by suction air. The pre-consolidation of the filament batt is performed by means of hot air.

The energy transferred onto the filament batt is controlled in a way that the filaments are only partly softened or pre-melted to generate good cohesion between individual filaments. Having achieved good filament cohesion, the filament batt can be transported on the formation belt without further help from any other device and without being influenced or destroyed/damaged by the transportation forces. This pre-consolidation process is also sufficient enough to run the filament batt into another lay down zone on a multi beam production line. The energy transferred to the filaments is not sufficient to activate the shrinkage of the filaments.

The method of the invention describes the balance of the pre-consolidation parameter, pre-consolidation temperature, pre-consolidation air speed and pre-consolidation time. Pre-consolidation time is understood to be the time during which the filament batt is treated by the pre-consolidation air.

Pre-consolidation time for the batt is recommended to be between 1 and 10000 ms, preferably between 2 and 1000 ms and most preferably between 4 and 200 ms.

Pre-consolidation air speed used in this pre-consolidation device is adjustable between 0.1 and 10 m/s, preferably in between 0.8 and 4 m/s. It is recommended that the pre-consolidation temperature of the pre-consolidation is between 80° C. and 200° C., preferably between 100° C. and 180° C. In one embodiment, the pre-consolidation temperature is 90° C. to 150° C., in particular 110° C. to 140° C. According to a preferred embodiment, the nonwoven layer of bicomponent filaments has a core component made of polyethylene terephthalate (PET) and a sheath component of a polyolefin particularly polyethylene or polypropylene, where the pre-consolidation temperature is preferably 110° C. to 160° C., and in particular 120° C. to 150° C. In one embodiment, the nonwoven layer comprises of bicomponent filaments, the core component made of polyethylene terephthalate (PET) and the sheath component of polyethylene terephthalate copolymer (CoPET), for which the pre-consolidation temperature is preferably 110° C. to 180° C. When the nonwoven layer is comprised of bicomponent filaments having a core component made of polylactic acid (PLA) and a sheath component of a polyolefin, in particular from a polyethylene or polypropylene, the pre-consolidation temperature is preferably 80° C. to 130° C.

Further down the production line from the diffuser, the filament batt is transported into at least one activation unit (10). The filaments are activated by means of hot air. It is understood that the actual shrinkage of the shrinkable component of the filament is a function of the temperature of the shrinkable component of the filament and also the duration of the temperature exposition. The speed of the shrinkage process depends on the temperature of the shrinkable component of the filament. In this invention the process is controlled in a way that the shrinkage is introduced slowly, so the forces introduced into the filament batt from the shrinkage are lower than the cohesion forces between the filaments.

The result of this process control is a cohesive and uniform nonwoven fabric structure with a reduced filaments structure density, which also results in an increased thickness of the nonwoven.

One embodiment of the invention is to join the process steps of pre-consolidation and activation by controlling the pre-consolidation and/or activation time, the pre-consolidation and/or activation air speed and the pre-consolidation and/or activation temperature in a combined pre-consolidation and activation device.

The innovative method describes the balance of the activation parameters: activation temperature, activation air speed and activation time. The activation time is understood as the time during which the filament batt is treated by the activation air. These parameters can be varied in the mentioned ranges in order to react to the potential shrinkage level in the filaments as well as to set the ideal combination between activation time, activation temperature and activation air speed.

The activation time for the batt is recommended between 20 and 5000 ms, preferably between 30 and 3000 ms and most preferably between 50 and 1000 ms The activation air speed used in this activation unit is adjustable between 0.1 and 2.5 m/s, preferably between 0.3 and 1.5 m/s. It is recommended that the activation temperature of the thermal activation is between 80° C. and 200° C., preferably between 100° C. and 160° C. In one embodiment, the activation temperature is 90° C. to 140° C., in particular 110° C. to 130° C. According to a preferred embodiment, the nonwoven layer of bicomponent filaments has a core component made of polyethylene terephthalate (PET) and a sheath component of a polyolefin particularly polyethylene or polypropylene, the activation temperature is preferably 90° C. to 140° C. and in particular 100° C. to 140° C. In one embodiment, the nonwoven layer comprises of bicomponent filaments, the core component made of polyethylene terephthalate (PET) and the sheath component of polyethylene terephthalate copolymer (CoPET), the activation temperature is preferably 120° C. to 160° C. When the nonwoven layer comprises of bicomponent filaments having a core component made of polylactic acid (PLA) and a sheath component made of a polyolefin in particular polyethylene or polypropylene, the activation temperature is preferably 80° C. to 140° C. The innovative method of this application prescribes a final bonding procedure of treating the filament batt with hot air in a bonding device (3). In the bonding device the filament batt of a single layer and/or more layers are bonded together without reducing the thickness of the filament batt significantly and having almost no bonding gradient throughout the thickness of the nonwoven. The remaining thickness and the resilience of the nonwoven is influenced by the bonding temperature since the bonding temperature should be high enough to achieve the needed bonds between the nonwoven fibers, without softening and collapsing the filament batt. In the bonding device, the bonding temperature and forces applied to the filament batt need to be adapted to the required process effect of low softening and low forces but sufficient to affect the integrity of the nonwoven filament batt. This can be achieved in multiple different devices like an Omega drum bonding device, a flat belt bonding device as well as a multiple drum bonder.

The bonded nonwoven is finally wound up on a winder (11). In case surface properties of the nonwoven need to be modified for example to achieve improved fluid transportation or wicking performance a spraying device or kiss roll is placed either in between the forming belt and the final bonding device or in between the final bonding device and the winder.

One embodiment of the invention is to connect the process steps of activation and bonding by controlling the activation and/or bonding time, activation and/or bonding air speed and activation and/or bonding temperature in the bonding device The method of the invention describes the balance of the bonding parameter bonding temperature, bonding air speed and bonding time. The bonding time is understood to be the time during which the filament batt is treated with the bonding air. These parameters can be varied in the mentioned ranges in order to react to the bonding potential of the filament batt as well as to achieve the ideal combination in between bonding time, bonding temperature and bonding air speed.

The bonding time for the batt is recommended between 200 and 20000 ms, preferably between 200 and 15000 ms and most preferably between 200 and 10000 ms.

The bonding air speed used in this bonding unit device is adjustable between 0.2 and 4.0 m/s, preferably between 0.4 and 1.8 m/s. It is recommended that the bonding temperature for thermal bonding is between 100° C. and 250° C., preferably between 120° C. and 220° C. In one embodiment, the bonding temperature is 90° C. to 140° C., in particular 110° C. to 130° C. According to a preferred embodiment, the nonwoven layer of bicomponent filaments has a core component made of polyethylene terephthalate (PET) and a sheath component from a polyolefin, particularly polyethylene or polypropylene; the bonding temperature is preferably 90° C. to 140° C. and in particular 100° C. to 140° C. In one embodiment, the nonwoven layer is comprised of bicomponent filaments, the core component is made from polyethylene terephthalate (PET) and the sheath component is made from polyethylene terephthalate copolymer (Co-PET), the bonding temperature is preferably 140° C. to 230° C. When the nonwoven layer is comprised of bicomponent filaments having a core component made from polylactic acid (PLA) and a sheath component made from a polyolefin, in particular from a polyethylene or polypropylene, the bonding temperature is preferably 80° C. to 140° C. The mentioned temperature ranges can be used in different discrete steps, so that the bonding air temperature as well as the bonding air speed remain within the mentioned range but in different zones of the bonding device at different levels.

The invention is based on the finding that a nonwoven fabric according to the invention can on the one hand be designed to be relatively bulky and thus exhibit a relatively large thickness, whilst on the other hand, nevertheless, retain satisfactory stability. Layer according to the invention have an excellent resilience after being subjected to a load or a pressure load. These advantageous properties can be achieved at relatively low basis weights of the nonwoven fabric.

The method of the invention is further characterized by the advantage that, a continuous production of the nonwoven fabric at relatively high production speeds without interruption of the production process is possible in a simple manner. The parameters for the production of the nonwoven fabric are highly variable and flexible, adjustable during the process and therefore variable end products can be produced without interrupting the production process. Also, pre-consolidation, activation and bonding steps can be easily varied with respect to the parameters.

The method of the invention can be performed in a simple way "inline", whilst still being able to be easily performed "offline" if necessary. Thus, the pre-consolidation, activation of shrinkage, and the final bonding can be uncoupled without any problems from actual laminate production. In summary, it should be noted that an innovative fabric having a very advantageous 3D structured surface with high volume and large thickness can be produced with satisfactory compression strength of the fabric in a simple, inexpensive and cost-effective manner. Various parameters of the nonwoven fabric or of the resulting nonwoven layer are variable and flexibly adjustable during the production process.

EXAMPLES

According to the invention, a layer can be produced, for example, on a laboratory line at UTB Zlin Centre of Polymer Systems Czech Republic. The laboratory line model LBS-300 is able to produce spunbond or meltblown fibers in mono or bico compositions. Its extrusion system, consisting of two extruders is able to heat polymers up to 450° C. Spunbond fibers can be produced using a spunbond die containing 72 holes (0.35 mm diameter; 1.4 mm length) on a square area of 6×6 cm. There are several possible bicomponent die configurations—core/sheath, side/side, segmented pie or islands-in-the-sea. The system is open; stretching air pressure in the inlet system is available up to 150 kPa. Filaments can be collected as they are or can be laid down on a belt at speeds from 0.7 to 12 m/min. The final product width is up to 10 cm. The total throughput rate can be set from 0.02 to 2.70 kg/h. The final basis weight of the product can be set between 30 and 150 g/m2. There is an option to bond the batt using a calendar roll at a temperature of up to 250° C. This laboratory line was used to produce layers described in examples 1-4.

To model air-through-bonding at the laboratory (examples 1-4), a standard stationary oven was used. Due to the very different heat transfer conditions present at the oven with a static atmosphere and the air stream forced to go through the fabric, and due to the heat loss during the opening and closing the oven, the activation time was set to 5 minutes.

Example 1—According to the Invention

The nonwoven consists of bicomponent filaments with a noncrimpable cross-section layout, core/sheath type, where the core/sheath mass ratio is 70:30, the core is formed using PLA (Ingeo from Nature Works) and the sheath is formed using PP (Tatren HT 2511 from Slovnaft). The nonwoven was produced on a laboratory line at UTB Zlin, Centre of Polymer Systems. The core extruder was heated up to 240° C. (3 zones heated to 195° C., 220° C. and 240° C. respectively), the sheath extruder was heated up to 235° C. (3 zones heated to 200° C., 215° C. and 235° C. respectively). The spinning beam temperature was set to 240° C. Polymer throughput was set to 0.25 g/min/capillary. Filaments were cooled with an air temperature of 20° C. The inlet pressure is shown in Table 2, with Examples 1A, 1C, 1E and 1F having an inlet pressure of 100 kPa, Example 1B having an inlet pressure of 50 kPa, and Example 1D having an inlet pressure of 150 kPa. Fibers were collected on a running belt; the batt gsm was set to 130 g/m2. The batt from the belt was cut into test samples of the size 10×7 cm. The samples were carefully moved to a separate oven and activated for a period of 5 minutes at a set temperature. These temperatures for each of Examples 1A-1F are also shown in Table 2.

TABLE 2

| | Example | | | | | |
|---|---|---|---|---|---|---|
| | 1A | 1B | 1C | 1D | 1E | 1F |
| material composition | | | PLA/PP | | | |
| oven temperature (° C.) | 100° C. | | 120° C. | | 140° C. | 160° C. |

TABLE 2-continued

| | Example | | | | | |
|---|---|---|---|---|---|---|
| | 1A | 1B | 1C | 1D | 1E | 1F |
| inlet pressure (kPa) | 100 | 50 | 100 | 150 | 100 | 100 |
| draw down ratio | 215 | 215 | 215 | 202 | 215 | 215 |
| filament speed [m/min] | 4 889 | 4 884 | 4 889 | 4 582 | 4 889 | 4 889 |
| activation change in fabric thickness | +100% | +60% | +133% | +96% | +155% | +137% |
| activation change in fabric length | −3% | −5% | −5% | −4% | −3% | −6% |
| activation change in fabric width | −3% | −3% | −2% | −2% | −4% | −3% |
| resilience * 100% | 37 | 27 | 35 | 23 | 36 | 34 |
| recovery * 100% | 98 | 98 | 98 | 97 | 98 | 98 |
| Structural softness | 568 | 378 | 641 | 254 | 587 | 578 |

Examples 1B, 1C and 1D demonstrate the possibility of controlling the shrinkage level by the size of fiber drawing force (inlet pressure). The cooling was the same for all three examples. Not to be bound by theory, we believe that the drawing force can help to induce a range of semistable crystalline states of the filament, some of which are more desirable for increasing thickness than others. When the drawing force is weaker, the resulting fiber can provide a relatively low toughness, which can then result in a lower final thickness of the web. On the other hand, when the drawing force is strong, the induced crystallization is set so that its volume changes and thus the shrinkage force during activation is lower, which again results in a lower final thickness. When the drawing force is just right, as shown in the Example 1C, the final fabric thickness and also the structural softness is the highest. Optimal conditions may be achieved by tuning the filament speed and the draw down ratio.

Examples 1A, 1C, 1E and 1F present the possibility to control the shrinkage level by the activation temperature. For these exact conditions, it can be seen that the best final thickness has the sample activated at 140° C. (+155%), however, the material according the invention is complex and the key evaluation parameter is structural softness, the very best sample being activated at 120° C.

Example 2—According to the Invention

The nonwoven fabric consists of bicomponent filaments with a noncrimpable cross-section layout, core/sheath type, where the core/sheath mass ratio is 70:30, the core is formed using PET (Type 5520 resin from Invista) and the sheath is formed using PP (Tatren HT 2511 from Slovnaft). The nonwoven was produced on a laboratory line at UTB Zlin, Centre of Polymer Systems. The core extruder was heated up to 340° C. (3 zones heated to 340° C., 335° C. and 325° C. respectively), the sheath extruder was heated up to 235° C. (3 zones heated to 200° C., 215° C. and 235° C. respectively). The spinning beam temperature was set to 305° C. Polymer throughput was set to 0.25 g/min/capillary. Filaments were cooled with an air temperature of 20° C. The inlet pressure is shown in Table 3. Fibers were collected on a running belt; the batt gsm was set to 75 g/m2. The batt from the belt was cut into test samples of the size 10×7 cm. Samples were carefully moved to a separate oven and activated for 5 minutes at a set temperature. The temperatures are shown in Table 3, with different temperatures corresponding to Examples 2A-2F.

Example 3—According to the Invention

The nonwoven consists of bicomponent filaments with a noncrimpable cross-section layout, core/sheath type, where the core/sheath mass ratio is 70:30, the core is formed using PET (Type 5520 resin from Invista) and the sheath is formed using a blend of 95% PP (Tatren HT 2511 from Slovnaft) and 5% of white masterbatch (CC10084467BG from PolyOne). The nonwoven was produced on a laboratory line at UTB Zlin, Centre of Polymer Systems. The core extruder was heated up to 340° C. (3 zones heated to 340° C., 335° C. and 325° C. respectively), the sheath extruder was heated up to 235° C. (3 zones heated to 200° C., 215° C. and 235° C. respectively). The spinning beam temperature was set to 305° C. Polymer throughput was set to 0.25 g/min/capillary. Filaments were cooled with an air temperature of 20° C. The inlet pressure is shown in Table 3. Fibers were collected on a running belt; the batt gsm was set to 75 g/m2. The batt from the belt was cut into test samples of the size 10×7 cm. Samples were carefully moved to a separate oven and activated for 5 minutes at a set temperature. The temperatures are shown in Table 3.

Example 4—Comparative Example

The nonwoven consists of bicomponent filaments with a noncrimpable cross-section layout, core/sheath type, where both core and sheath were formed using PET (Type 5520 resin from Invista). The nonwoven was produced on a laboratory line at UTB Zlin, Centre of Polymer Systems. The extruders were heated up to 340° C. (3 zones heated to 340° C., 335° C. and 325° C. respectively). The spinning beam temperature was set to 305° C. Polymer throughput was set to 0.25 g/min/capillary. Filaments were cooled with an air temperature of 20° C. The inlet pressure is shown in Table 3. Fibers were collected on a running belt; the batt gsm was set to 75 g/m2. The batt from the belt was cut into test samples of the size 10×7 cm. Samples were carefully moved to a separate oven and activated for 5 minutes at a set temperature. The temperatures are shown in Table 3.

TABLE 3

| | Example | | | | | | | |
|---|---|---|---|---|---|---|---|---|
| | 2A | 2B | 2C | 2D | 2E | 2F | 3 | 4 |
| material composition | | | PET/PP | | | | PET/ (PP + white) | PET/ PET |
| oven temperature (° C.) | 100° C. | 120° C. | 140° C. | 150° C. | 160° C. | | 140° C. | |
| inlet pressure (kPa) | | | 50 | | | 100 | 100 | 100 |
| draw down ratio | 214 | 214 | 214 | 214 | 214 | 224 | 224 | 253 |
| filament speed [m/min] | 4 469 | 4 469 | 4 469 | 4 469 | 4 469 | 4 696 | 4 088 | 4 766 |
| activation change in fabric thickness | +19% | +31% | +51% | +47% | +39% | +103% | +105% | +222% |
| activation change in fabric length | −5% | −6% | −8% | −8% | −7% | −15% | −14% | −63% |
| activation change in fabric width | −5% | −2% | −5% | −6% | −6% | −15% | −15% | −63% |
| resilience * 100% | 2 | 33 | 33 | 23 | 12 | 40 | 41 | — |
| recovery * 100% | 95 | 97 | 99 | 98 | 99 | 98 | 98 | — |
| Structural softness | 13 | 306 | 321 | 223 | 88 | 397 | 400 | — |

Examples 2C and 3 demonstrate the same principle as examples 1B-D above. Examples 2A-F demonstrate the possibility of controlling the shrinkage level using the activation temperature. For these exact conditions, it is evident that the best final thickness was on the sample activated at 140° C. (+51%) and the same temperature was also the best from the structural softness point of view.

Example 3 and comparative example 4 demonstrate the importance of correct sheath material in the material according to the invention. It can be clearly seen, that the PET/PET material has a significantly different behavior during activation, which leads to a different shrinkage level (see FIG. 4). The sample according to the invention increased its volume by 47% and also provided good resilience and recovery values. In contrast, the PET/PET sample had decreased in volume by −56% and shrunk into a hard slightly bent piece, on which it was not possible to measure the resilience or recovery values. Also the filament length measurement was not possible.

It shall be noted, that the CD and MD shrinkage level is below 10 percent for examples 2A-F, as is the case with the abovementioned examples 1A-E. In contrast, the increase of thickness is much higher than the decrease in the CD and MD directions. Examples 2F and 3 provide very good values of structural softness and also an acceptable level of CD and MD shrinkage (15%).

It shall be also noted, that the PET used in examples 2-4 contained a small amount of $TiO_2$ (used as a mating agent by the polymer producer). In contrast, the PLA used in example 1 does not contain any $TiO_2$.

According to an exemplary embodiment of the invention, one layer or two layers can be produced inline, for example, on a Reifenhauser Reicofil pilot line at Troisdorf, Germany. This line was used to produce the nonwovens described in examples according to invention below, i.e. Examples 5, 6, 8, 9, 10, 11 with following standard setting:

Pre-consolidation air speed 2.3 [m/s]

Activation air speed 1.3 [m/s]

Bonding air speed 1.3 [m/s]

Quenching air temperature 20 [° C.].

The pilot line is equipped with two BiCo spunbond beams, each of them equipped with two extruders supplying a BiCo coat hanger die. The extrusion system allows temperatures up to 350° C. to process a wide variety of polymers within a specific total throughput range per beam of 80 to 450 kg/h/m. Multiple spinnerets are available with different capillary densities as well as capillary geometries. Spin packs having a HILLS melt distribution system are used to form in addition to the standard cross section described in this invention almost every cross section to imagine on a 1.1 m wide spinneret. The devices for cooling, stretching and formation are today's industry-reference covering a wide range of cooling and drawing conditions ensuring an excellent uniform filament batt. The forming belt runs up to 400 m/min production speed. The nonwoven layer from the first spunbond beam passes optional pre-consolidation, activation and/or bonding devices inline before the layer from the second beam is stacked on top of the first one. The second beam is equipped with similar inline-equipment for optional pre-consolidation, activation and bonding as the first one. The pre- or finally bonded product is wound up on an inline slitter-winder or might be inline bonded on a drum bonder prior to winding. Surfactant treatment by a kiss roll to modify surface properties of the nonwoven is available inline or offline.

Example 5—According to the Invention

The nonwoven was produced on one bicomponent spunbond beam round shape core/sheath type. The core/sheath mass ratio was 70/30. The core was produced from PET (Type 5520 resin from Invista) and the sheath was produced using PE (ASPUN 6834 from Dow). The process conditions and final fabric parameters for each of Examples 5A-5D are shown in the Table 4 below. The activation and the bonding were done on a single piece of equipment with a set activation and bonding zone.

TABLE 4

| | Example | | | |
|---|---|---|---|---|
| | 5A | 5B | 5C | 5D |
| Composition polymer plastic group A/ polymer plastic group B | PET/PE | PET/PE | PET/PE | PET/PE |
| BiCo cross section polymer plastic group A/ polymer plastic group B | C/S | C/S | C/S | C/S |
| layer count | 1 | 1 | 1 | 1 |
| capillary shape | round | round | round | round |
| spinneret capillary density [1000/m] | 1.1 | 1.1 | 1.1 | 1.1 |
| melt temperature polymer plastic group A [° C.] | 286 | 286 | 286 | 286 |
| melt temperature polymer plastic group B [° C.] | 267 | 267 | 267 | 267 |
| drawing force level | very low | low | medium | high |
| suction force level | low | medium | medium | medium |
| cooling air/polymer ratio | 35.2 | 37.9 | 41.0 | 42.7 |
| draw down ratio | 443 | 483 | 625 | 665 |
| filament speed [m/min] | 3496 | 3810 | 4930 | 5253 |
| pre-consolidation time [s/1000] | 68 | 68 | 68 | 68 |
| pre-consolidation temperature [° C.] | 130 | 130 | 130 | 130 |
| activation time [s/1000] | 682 | 682 | 682 | 682 |
| activation temperature [° C.] | 135 | 135 | 135 | 135 |
| bonding time [s/1000] | 2455 | 2455 | 2455 | 2455 |
| bonding temperature [° C.] | 130 | 130 | 130 | 130 |
| Basis weight [gsm] | 62 | 59 | 64 | 64 |
| Apparent fiber diameter [µm] | 38 | 36 | 32 | 31 |
| Resilience * 100% | 35 | 37 | 37 | 35 |
| Compressibility [mm]/basis weight [gsm] | 0.0111 | 0.0113 | 0.0101 | 0.0089 |
| Recovery * 100% | 99 | 98 | 99 | 99 |
| Thickness [mm] | 1.96 | 1.83 | 1.72 | 1.63 |
| Structural softness [$m^4mm^2g^{-2}$] | 346 | 342 | 270 | 224 |
| % of fibres having the length of the filament to the length of the fabric ratio higher than 1.2:1 | 74.94 | 80.26 | 70.43 | 66.75 |
| % of fibres having the length of the filament to the length of the fabric ratio higher than 1.5:1 | 61.86 | 66.25 | 57.14 | 55.10 |
| % of fibres having the length of the filament to the length of the fabric ratio lower than 2.5:1 | 72.86 | 77.41 | 67.93 | 64.38 |

Examples 5A—D demonstrate the importance of the cooling air/polymer ratio, draw down ratio and filament speed on the final fabric properties. It can be seen that with increased drawing and cooling, the fabric thickness, the fiber diameter and also the structural softness decrease. On the other hand, the mechanical properties of the final product increase.

Example 6—According to the Invention

The nonwoven fabric was produced on two subsequent bicomponent spunbond beams, round shape core-sheath type. The core/sheath mass ratio was 70/30. The core was produced from PET (Type 5520 resin from Invista) and the sheath was produced using PE (ASPUN 6834 from Dow). The process conditions and final fabric parameters for each of Examples 6A-6D are shown in Table 5 below. Activation and bonding were done on a single piece of equipment with a set activation and bonding zone.

TABLE 5

| | Example | | | |
|---|---|---|---|---|
| | 6A | 6B | 6C | 6D |
| Composition polymer plastic group A/ polymer plastic group B | PET/PE | PET/PE | PET/PE | PET/PE |

TABLE 5-continued

| | Example | | | |
|---|---|---|---|---|
| | 6A | 6B | 6C | 6D |
| BiCo cross section polymer plastic group A/ polymer plastic group B | C/S | C/S | C/S | C/S |
| layer count | 2 | 2 | 2 | 2 |
| capillary shape | round | round | round | Round |
| spinneret capillary density [1000/m] | 1.1 | 1.1 | 1.1 | 1.1 |
| melt temperature polymer plastic group A [° C.] | 281 | 281 | 281 | 281 |
| melt temperature polymer plastic group B [° C.] | 266 | 266 | 266 | 266 |
| drawing force level | medium | medium | medium | Medium |
| suction force level | low | low | low | Low |
| cooling air/polymer ratio | 38.0 | 38.0 | 37.9 | 37.9 |
| draw down ratio | 465 | 478 | 551 | 517 |
| filament speed [m/min] | 3669 | 3773 | 4343 | 4048 |
| pre-consolidation time [s/1000] | 35 | 23 | 17 | 15 |
| pre-consolidation temperature [° C.] | 130 | 130 | 130 | 130 |
| activation time [s/1000] | 349 | 231 | 169 | 150 |
| activation temperature [° C.] | 135 | 135 | 135 | 135 |
| bonding time [s/1000] | 1256 | 831 | 610 | 540 |
| bonding temperature [° C.] | 130 | 130 | 134 | 134 |
| Basis weight [gsm] | 60 | 40 | 30 | 26 |
| Apparent fiber diameter [μm] | 37 | 36 | 34 | 35 |
| Resilience * 100% | 32 | 35 | 19 | 11 |
| Compressibility [mm]/basis weight [gsm] | 0.0104 | 0.0122 | 0.0067 | 0.0035 |
| Recovery * 100% | 99 | 97 | 97 | 97 |
| Thickness [mm] | 1.9 | 1.4 | 1.0 | 0.9 |
| Structural softness [$m^4mm^2g^{-2}$] | 331 | 407 | 225 | 110 |
| % of fibres having the length of the filament to the length of the fabric ratio higher than 1.2:1 | 78.96 | 56.97 | 42.30 | 34.98 |
| % of fibres having the length of the filament to the length of the fabric ratio higher than 1.5:1 | 65.18 | 47.03 | 34.92 | 28.88 |
| % of fibres having the length of the filament to the length of the fabric ratio lower than 2.5:1 | 76.16 | 54.96 | 40.80 | 33.74 |

Example 7—Comparative Example

The nonwoven fabric consists of bicomponent filaments with a crimpable cross-section layout, round eccentric core/sheath type, where the core is from PET and sheath from PE. The fabric was hot-air bonded. The fabric parameters for each of Examples 7A-7C are shown in Table 6 below.

TABLE 6

| | Example | | |
|---|---|---|---|
| | 7A | 7B | 7C |
| Composition polymer plastic group A/ polymer plastic group B | PET/PE | PET/PE | PET/PE |
| BiCo cross section polymer plastic group A/ polymer plastic group B | eC/S | eC/S | eC/S |
| layer count | 1 | 1 | 1 |
| capillary shape | round | round | round |
| Basis weight [gsm] | 51 | 83 | 33 |
| Resilience * 100% | 15 | 17 | 17 |
| Compressibility [mm]/basis weight [gsm] | 0.0028 | 0.0033 | 0.0036 |
| Recovery * 100% | 98 | 99 | 97 |
| Thickness [mm] | 0.9 | 1.6 | 0.7 |
| Structural softness [m4mm2g−2] | 52 | 63 | 74 |

Figure 9:
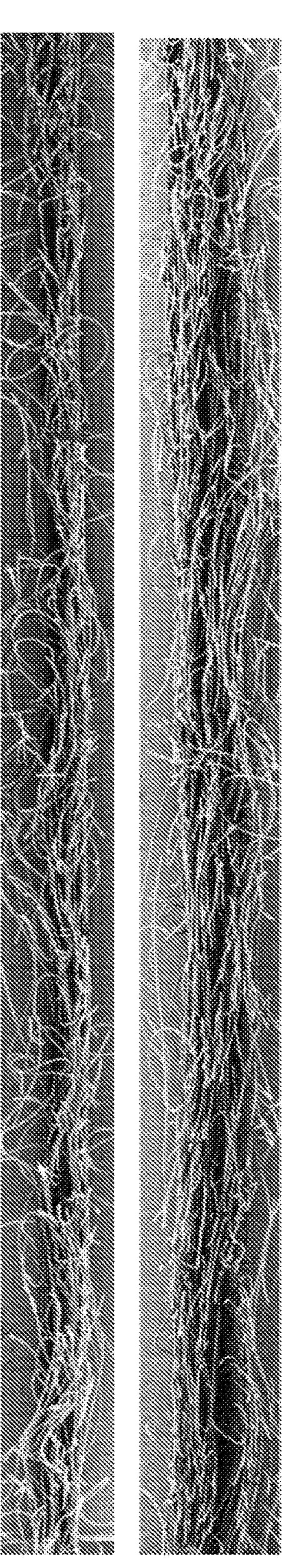
FIG. 9: Fabric cross-section—Examples 5A+D (according to the invention)

Examples 7A-C represent a one-layer nonwoven fabric with comparable polymer composition. However, the fibers have a crimpable crossection and crimps, as is visible on the fabric cross-section in FIG. 8 as compared with the cross-sections of examples according to the invention (5A+D)—FIG. 9. The structural softness of the examples is, compared to examples 5 and 6 significantly lower, as well as the fabric thickness.

Example 8—According to the Invention

The nonwoven fabric was produced from two subsequent bicomponent spunbond beams, round shape core-sheath type. The core/sheath mass ratio was 70/30. The core was produced from PET (Type 5520 resin from Invista) and the sheath was produced using coPET (type 701k from Invista). The process conditions and final fabric parameters for each of Examples 8A and 8B are shown in Table 7 below. The activation and the bonding were performed inline on the belt with separate devices for activation and bonding.

Example 9—According to the Invention

The nonwoven was produced on two subsequent bicomponent spunbond beams, round shape core-sheath type. The core/sheath mass ratio was 70/30. The core was produced from PET (Type 5520 resin from Invista) and the sheath was produced using coPET (type 701k from Invista). The process conditions and final fabric parameters for each of Examples 9A-9C are shown in Table 7 below. The activation was performed in a single step, the bonding in a second step on different equipment. In the case of examples 9A+B, the bonding was done immediately after activation inline on a drum. In the case of Example 9C, the bonding was done on different equipment several days after activation offline on a drum.

TABLE 7

| | Example | | | | |
|---|---|---|---|---|---|
| | 08A | 08B | 09A | 09B | 09C |
| Composition polymer plastic group A/ polymer plastic group B | PET/ CoPET | PET/ CoPET | PET/ CoPET | PET/ CoPET | PET/ CoPET |
| BiCo cross section polymer plastic group A/ polymer plastic group B | C/S | C/S | C/S | C/S | C/S |
| layer count | 2 | 2 | 2 | 2 | 2 |
| capillary shape | round | round | round | round | round |
| spinneret capillary density [1000/m] | 1.1 | 1.1 | 1.1 | 1.1 | 1.1 |
| melt temperature polymer plastic group A [° C.] | 279 | 279 | 276 | 275 | 279 |
| melt temperature polymer plastic group B [° C.] | 276 | 276 | 275 | 275 | 276 |
| drawing force level | high | high | high | high | high |
| suction force level | high | high | medium | medium | high |
| cooling air/polymer ratio | 41.1 | 41.1 | 41.1 | 41.1 | 41.1 |
| draw down ratio | 675 | 630 | 649 | 619 | 711 |
| filament speed [m/min] | 4846 | 4521 | 4656 | 4441 | 5104 |
| pre-consolidation time [s/1000] | 38 | 50 | 46 | 35 | 25 |
| pre-consolidation temperature [° C.] | 160 | 160 | 160 | 160 | 160 |
| activation time [s/1000] | 375 | 500 | 462 | 349 | 250 |
| activation temperature [° C.] | 140 | 140 | 150 | 150 | 140 |
| bonding time [s/1000] | 1350 | 1800 | 1522 | 1151 | 5376 |
| bonding temperature [° C.] | 155 | 155 | 215 | 219 | 218 |
| Basis weight [gsm] | 59 | 79 | 76 | 58 | 38 |
| Apparent fiber diameter [μm] | 31 | 32 | 31 | 32 | 30 |
| Resilience * 100% | 28 | 23 | 12 | 16 | 17 |
| Compressibility [mm]/basis weight [gsm] | 0.0086 | 0.0063 | 0.0023 | 0.0037 | 0.0046 |
| Recovery * 100% | 100 | 99 | 100 | 100 | 97 |
| Thickness [mm] | 1.8 | 2.2 | 1.5 | 1.3 | 1.0 |
| Structural softness [$m^4mm^2g^{-2}$] | 269 | 168 | 46 | 82 | 118 |
| % of fibres having the length of the filament to the length of the fabric ratio higher than 1.2:1 | 74.65 | 88.48 | 61.87 | 53.73 | 41.52 |
| % of fibres having the length of the filament to the length of the fabric ratio higher than 1.5:1 | 61.62 | 73.04 | 51.08 | 44.35 | 34.28 |
| % of fibres having the length of the filament to the length of the fabric ratio lower than 2.5:1 | 72.00 | 85.33 | 59.68 | 51.82 | 40.05 |

Examples 8 and 9 demonstrate the importance of the bonding conditions. Example 8 focuses on high structural softness. The sheath polymer melting temperature is higher than in previous examples, thus the optimal bonding temperature is higher than the core activation temperature. The used bonding temperature (155° C.) is close to the optimal activation temperature, not reaching the optimal bonding level. Also the mechanical properties are at a lower level. In contrast, Example 9 focuses on the optimal bonding level with better mechanical properties, but lower thickness and structural softness. Example 9C was bonded offline, simulating the capability to separate the process steps "activation" and "bonding" from each other. After activation the product is wound up and transported to another location. There it is unwound and the final bonding is done.

Other than bonding temperature and time, other parameters, especially the pressure during the bonding phase (including the pressure from the air throughput, the pressure from the tension of the nonwoven web, the pressure from auxiliary guide rollers, etc.), can also influence the final thickness and reduce the structural softness. The difference between examples 9A+B and 9C represents not only the online/offline possibility, but also the influence of different bonding settings.

Example 10—According to the Invention

The nonwoven was produced on two subsequent bicomponent spunbond beams, trilobal shape core-sheath type. The core/sheath mass ratio was 70/30. The core was produced from PET (Type 5520 resin from Invista) and the sheath was produced using coPET (type 701k from Invista). The process conditions and final fabric parameters are shown in Table 8 below. The activation and the bonding were performed on a single piece of equipment with a set activation and bonding zone.

Example 11—According to the Invention

The nonwoven was produced on two subsequent bicomponent spunbond beams, round shape core-sheath type. The core/sheath mass ratio was 70/30. The core was produced from PET (Type 5520 resin from Invista) and the sheath was produced using coPET (Type RT5032 from Trevira). The process conditions and final fabric parameters for each of Examples 11A and 11B are shown in Table 8 below. The activation and the bonding were performed on a single piece of equipment with a set activation and bonding zone.

TABLE 8

| | Example | | |
|---|---|---|---|
| | 10 | 11A | 11B |
| Composition polymer plastic group A/ polymer plastic group B | PET/ CoPET | PET/ CoPET | PET/ CoPET |
| BiCo cross section polymer plastic group A/ polymer plastic group B | C/S | C/S | C/S |
| layer count | 1 | 2 | 2 |
| capillary shape | trilobal | round | Round |
| spinneret capillary density [1000/m] | 1.1 | 3.21 | 3.21 |
| melt temperature polymer plastic group A [° C.] | 276 | 299 | 300 |
| melt temperature polymer plastic group B [° C.] | 275 | 277 | 278 |
| drawing force level | high | low | Low |
| suction force level | medium | low | Low |
| cooling air/polymer ratio | 38.7 | 28.1 | 28.2 |
| draw down ratio | 1947 | 386 | 403 |
| filament speed [m/min] | 3607 | 3759 | 3925 |
| pre-consolidation time [s/1000] | 92 | 56 | 42 |
| pre-consolidation temperature [° C.] | 120 | 130 | 130 |
| activation time [s/1000] | 923 | 561 | 417 |
| activation temperature [° C.] | 145 | 130 | 130 |
| bonding time [s/1000] | 3323 | 2019 | 1500 |
| bonding temperature [° C.] | 140 | 130 | 130 |
| Basis weight [gsm] | 56 | 60 | 80 |
| Apparent fiber diameter [μm] | 42 | 23 | 22 |
| Resilience * 100% | 39 | 25 | 23 |
| Compressibility [mm]/basis weight [gsm] | 0.0125 | 0.0081 | 0.0070 |
| Recovery * 100% | 98 | 98 | 99 |
| Thickness [mm] | 1.8 | 1.9 | 2.4 |
| Structural softness [$m^4mm^2g^{-2}$] | 395 | 253 | 204 |
| % of fibres having the length of the filament to the length of the fabric ratio higher than 1.2:1 | 73.17 | 78.64 | 97.34 |
| % of fibres having the length of the filament to the length of the fabric ratio higher than 1.5:1 | 60.84 | 64.91 | 80.35 |
| % of fibres having the length of the filament to the length of the fabric ratio lower than 2.5:1 | 71.09 | 75.84 | 93.88 |

Example 10 demonstrates the possibility of using filaments with a different non-round shape.

Example 11A+B demonstrates the possibility of also using a spinneret with higher capillary density.

Example 12—Comparative Example

The nonwoven samples chosen as comparative examples were produced by TWE group under the brand "TWE Hygiene". The nonwoven consists of short bicomponent fibers, core-sheath type, where the core is from PET and the sheath from PE (qualified guess of materials, no deep laboratory analysis of the materials of these samples has been made so far). The fabric was produced using carding technology, consolidated by hot-air-bonding.

The fabric parameters for each of Examples 12A-12C are shown in Table 9 below.

TABLE 9

| | Example | | |
|---|---|---|---|
| | 12A | 12B | 12C |
| Composition polymer plastic group A/ polymer plastic group B | PET/PE | PET/PE | PET/PE |
| Fabric name | TL 7 | TL 1 | TWE 286 |
| Technology | carded | carded | carded |
| Basis weight [gsm] | 97 | 67 | 23 |
| Resilience * 100% | 41 | 44 | 35 |
| Compressibility [mm]/basis weight [gsm] | 0.0082 | 0.0082 | 0.0065 |
| Recovery * 100% | 99 | 99 | 98 |
| Thickness [mm] | 1.9 | 1.2 | 0.4 |
| Structural softness [m4mm2g−2] | 161 | 151 | 120 |
| % of fibres having the length of the filament to the length of the fabric ratio higher than 1.2:1 | 53.4 | N/A | N/A |
| % of fibres having the length of the filament to the length of the fabric ratio higher than 1.5:1 | 23.9 | N/A | N/A |

TABLE 9-continued

| | Example | | |
|---|---|---|---|
| | 12A | 12B | 12C |
| % of fibres having the length of the filament to the length of the fabric ratio lower than 2.5:1 | 97.9 | N/A | N/A |

An objective of the present invention is to achieve a bulky nonwoven fabric that may be compressed with a rather low pressure and may also recover when freed. A person skilled in the art understands that modern carded materials, as a result of long-term development, may also be suitable. On the other hand, carded materials are produced from staple fibers and the high number of ends of these fibers across and along a nonwoven layer may be unwelcome for certain applications. Example 12A-C provides the properties of three commercially available carded fabrics specified for use in hygiene. Comparing this set of samples with the samples according to the invention with comparative polymer compositions, it can be seen that the carded materials have a slightly higher resilience, but due to their lower thickness, their compressibility is comparable or lower, so the real touch and feel of soft-loft is equal or better for materials according to the invention.

Testing Methodology

The "Basis weight" of a nonwoven web is measured according to the European standard test EN ISO 9073-1:1989 (conforms to WSP 130.1). There are 10 nonwoven web layers used for measurement, sample area size is 10×10 cm2.

The "Thickness" or "Caliper" of the nonwoven material is measured according to the European standard test EN ISO 9073-2:1995 (conforms to WSP 120.6) with following modification:

1. The material shall be measured on a sample taken from production without being exposed to higher strength forces or spending more than a day under pressure (for example on a product roll), otherwise before measurement the material must lie freely on a surface for at least 24 hours.

2. The overall weight of the upper arm of the machine including added weight is 130 g.

The "recovery" of the bulkiness after pressure herein refers to the ratio of thickness of the fabric after it was freed from the load to the original thickness of fabric. The thickness of the fabric is measured according to the EN ISO 9073-2:1995 using a preload force of 0.5 kPa).

The recovery measurement procedure consists of following steps:

1. Prepare fabric samples measuring 10×10 cm
2. Measure the thickness of 1 piece of fabric
3. Measure the thickness of a pile of 5 pieces of fabric using a preload force of 0.5 kPa (Ts)
4. Load the pile of 5 fabric sheets on to a thickness meter (2.5 kPa) for 5 minutes
5. Release the weight and wait for 5 minutes
6. Measure the thickness of pile of the 5 fabrics using a preload force of 0.5 kPa (Tr)
7. Calculate the recovery according to the following equation:

$$\text{Recovery} = Tr/Ts \text{ (no unit)}$$

Ts=thickness of fresh sample

Tr=thickness of recovered sample

The "compressibility" herein refers to the distance in mm by which the nonwoven is compressed by the load defined in "resilience" measurement. It can be also calculated as resilience (no unit)*thickness (mm). The "resilience" of a nonwoven is measured according to the European standard test EN ISO 964-1 with following modification:

1. The thickness of one layer of the fabric is measured.
2. A pile of fabric samples is prepared so that the total thickness is at least 4 mm, optimally 5 mm in total. The pile of fabrics contains at least 1 piece of fabric.
3. The thickness of the pile of fabric samples is measured
4. A force of 5N with loading speed of 5 mm/min is applied to the pile of nonwoven samples
5. The distance of the clamp movement is measured
6. Resilience is calculated according to the equation:

$$R \text{ (no unit)} = T1 \text{ (mm)}/T0 \text{ (mm)}$$

Or $$R\,(\%) = T1 \text{ (mm)}/T0 \text{ (mm)}*100\%$$

T1=distance of the clamp movement under the load 5N [mm]=how much was the pile of fabrics compressed T0=thickness (acc. EN ISO 9073-2:1995 using the preload force 1.06N) [mm]

The "length of the filament to the length of the fabric ratio" can be measured in three different ways:

a) The length of the filaments is measured by stretching them out so that they extend along a line without exhibiting crimps. The method is the better the lower the bonding is.

b) In a fabric bonded to a given level, it is not possible to use method a) to measure the length of the filaments, so that the following estimation may be used:

a. A picture of the assessed layer is provided in such a magnification that the fibers can be well seen
b. One single fiber is chosen and its path through the picture or at least through part of the picture is marked out
c. The length of fiber marked out on the picture is measured to estimate its real length
d. The length of the fabric, where the fiber is marked out is measured
e. The estimated length of the filament to the length of the fabric ratio (percentage) is calculated for at least 20 fibers.

c) In a fabric using the "Method for determining geometric fiber statistics for a nonwoven material", where:

a. The geometric representation of the fabric for analysis measures 8 mm in MD and 8 mm in CD, maintaining the full thickness of the sample in z-direction.
b. Only the fibers, that enter the cropped sample volume on one side and leave it at opposite side are relevant for the measurement
c. At least 20 filaments have to be measured
d. The length of the filament to the length of the fabric ratio (percentage) is calculated "The type of fiber cross-section" is known from the process conditions, defined by the fiber forming die. In the event that the process conditions are unknown, the following estimation can be used:

A sample of the fabric is taken and pictures of the cross-sections of at least 20 fibers are made. The cross-section is made on the free part of the fiber, not in the bonding point or in a place of contact with another fiber, where deformation can be expected. For each cross-section, the component surface is marked out on the image separately for each component. The centre of mass is determined for each component based on the centroid or geometric center determination of the planar object and its position is recorded using the Cartesian coordinate system with the centre [0; 0] in the geometrical centre of the fiber cross-section. The deflection (D) of centre of mass for each component in each fiber cross-section is calculated according to the following equation:

$$D=\text{absolute value } (x*y),$$

where x and y are the coordinates of centre of mass. When one of the x, y values is equal to 0 and not the other, the sample is discarded from evaluation)

The average value and standard deviation is calculated for each component.

The fiber is considered noncrimpable when the ((average deflection) plus (standard deviation)) to total fiber cross-section surface ratio is less than 5%.

The fiber is expected noncrimpable when the ratio ((average deflection) minus (standard deviation)) to total fiber cross-section surface ratio is less than 5%.

"Median fiber diameter" in a layer is expressed in SI units—micrometers (μm) or nanometers (nm). To determine the median, it is necessary to take a sample of the nonwoven fabric from at least three locations at least 5 cm away from each other. In each sample, it is necessary to measure the diameter of at least 50 individual fibers for each observed layer. It is possible to use, for example, an optical or electronic microscope (depending on the diameter of the measured fibers). In the event that the diameter of fibers in one sample varies significantly from the other two, it is necessary to discard the entire sample and to prepare a new one.

In the case of round fibers, the diameter is measured as a diameter of the cross-section of the fibers. In the event of any other shape of the fiber (e.g. hollow fiber or trilobal fiber), the cross-section surface shall be determined for each measured fiber and recalculated for a circle with same surface area. The diameter of this theoretical circle is the diameter of the fiber.

The measured values for each layer composed of all three samples are consolidated into a single set of values from which the median is subsequently determined. It applies that at least 50% of the fibers have a diameter less than or equal to the value of the median and at least 50% of the fibers have a diameter greater than or equal to the median. To identify the median of the given sample set of values, it is sufficient to arrange the values according to size and to take the value found in the middle of the list. In the event that the sample set has an even number of items, usually the median is determined as the arithmetic mean of the values in locations N/2 and N/2+1.

The "void volume" herein refers to the total amount of void space in a material relative to the bulk volume occupied by the material.

The bulk volume of the material is equal to the bulk volume of the nonwoven and can be calculated from fabric thickness (caliper) using the following equation:

$$\text{bulk volume } (m^3)=\text{caliper (mm)}/1000*1*1$$

The total amount of void space in a material can be calculated using to the equation:

$$\text{void space}=\text{bulk volume } (m^3)-\text{mass volume } (m^3)$$

The total mass volume can be calculated using to the equation:

$$\text{mass volume } (m^3)=\text{basis weight } (g/m^2)/1000/\text{mass density } (kg/m^3)$$

Where the mass density can be calculated from a known composition or measurement according to the norm ISO 1183-3:1999.

So the void volume can be calculated using the equation:

$$\text{Void volume } (\%)=1-(\text{basis weight } (g/m^2)*\text{caliper (mm)})/\text{mass density } (kg/m^3)*100\%$$

"Method to determine geometric fiber statistics for a nonwoven" In the following, we describe a software-based method to analyze a sample of a nonwoven material in order to characterize its geometric properties. The method uses a machine-learning approach to identify the individual fibers present in the sample followed by a geometric analysis of these fibers to obtain statistics suitable for characterizing the material. The results include the orientation and density distribution of the fibers. This analysis workflow was developed by Math2Market GmbH and is part of the GeoDict digital material laboratory.

Step 1: Obtain three-dimensional μCT image of sample

First, the nonwoven sample is digitized using a μCT scanner to obtain a 3D image. The 3D image consists of a uniform Cartesian grid where each grid cell (Volume Element, Voxel) stores the X-Ray attenuation of the sample at the corresponding location. The pore space typically shows the lowest attenuation (smallest gray-scale value) while the material phase exhibits larger values, depending on the material and the configuration of the μCT device.

Step 2: Segment μCT Image to Separate Material from Pore Space

For further analysis, the gray-scale image is noise-filtered using the Non-Local Means approach [1]. It is then binarized using a global threshold derived using Otsu's algorithm [2]. Binarization classifies each image voxel as containing either pore space or fiber material. Voxels with gray values below the threshold are classified as pore space. All other voxels are classified as fiber material. For both operations, noise filtering and thresholding, the ImportGeo module of the GeoDict software is used.

Step 3: Analyze Material Density Distribution

Furthermore, the material density distribution in z-direction is computed. For each slice of the image (at a given depth Z), the material density is computed as the number of white material voxels divided by the number of total voxels in the slice. This analysis is performed using the MatDict module of GeoDict.

Step 4: Apply a Neural Network to Identify Fiber Centerlines

The main challenge in identifying individual fibers in μCT images is that, after binarization, the fibers are not spatially separated at contact points. This can result in under-segmentation, where multiple objects (fibers) are erroneously classified as a single fiber. To separate the fibers, Math2Market GmbH has developed an approach to identify the centerline curves of the fibers. These centerlines are represented in a binary voxel image of the same size as the original image. In this image, voxels within about 1-2 voxels to a fiber's center are marked.

For this purpose, we have used a semantic segmentation approach using a neural network [3]. The image is analyzed by considering a 3D sliding input window which is moved over the image. For each input window, a smaller output window is defined which is centered on the input window. The neural network analyzes the binary voxel values in the input window and produces a prediction for each voxel of the output window. The predicted value determines if a voxel inside the output window is part of a centerline. By combining the results for all these output windows we obtain a binary image which classifies each material voxel in the original image. This image transformation is implemented by the FiberFind-AI module in GeoDict, utilizing Tensorflow [4].

Step 5: Create Training Data for the Neural Networks

For the purpose of training the neural network to implement the transformation described above, Math2Market GmbH has created several artificial 3D images of nonwoven materials using the stochastic FiberGeo structure generation module in GeoDict. This module generates an analytical geometric representation of fibers as a series of line segments. At the same time, it outputs a binary image of the fiber structure, comparable to the binarization result of Step 2.

By modifying the fiber diameter in the analytical representation to about 2-3 voxels, we can likewise obtain an image of the centerlines corresponding to the artificial fiber structure.

These pairs of images (fibers and centerlines) are then used to train the neural network to transform a fiber image to a centerline image. The network effectively learns to "shrink" the fibers down to their centerline curves.

Step 6: Trace Fiber Centerlines to Obtain Geometric Representation of Fibers

After reducing the fibers to their centerlines, we assume that the centerlines do not touch.

We then separate the individual centerlines from each other by analyzing the connected components of the centerline image, under the assumption that each component corresponds to the centerline of a single fiber. A connected component is defined as a subset of material voxels that all have the same color and that cannot be enlarged by adding any touching voxels of the same color.

For each centerline, we trace a curve through the set of voxels to obtain a geometric representation of the corresponding fiber in the form of a sequence of connected line-segments (a polyline). This step is also part of FiberFind-AI in GeoDict.

Step 7: Compute Orientation Distribution Histogram of Fibers

To obtain the orientation distribution in any plane (say, the XY plane), we first project each fiber line segment into that plane and compute the angle within the plane. Then, the orientation histogram is computed over the angle of all segments. Finally, this orientation histogram is visualized using a polar plot where the radius at a given angle is proportional to the frequency of occurrence of the corresponding orientation. This analysis is repeated for the remaining two planes (XZ and YZ).

[1] Buades, Antoni, Bartomeu Coll, and J-M. Morel. "A non-local algorithm for image denoising." Computer Vision and Pattern Recognition, 2005. CVPR 2005. IEEE Computer Society Conference on. Vol. 2. IEEE, 2005.

[2] Otsu, Nobuyuki. "A threshold selection method from gray-level histograms." IEEE transactions on systems, man, and cybernetics 9.1 (1979): 62-66.

[3] Noh, Hyeonwoo, Seunghoon Hong, and Bohyung Han. "Learning deconvolution network for semantic segmentation." Proceedings of the IEEE international conference on computer vision. 2015.

[4] Martin Abadi, Ashish Agarwal, Paul Barham, Eugene Brevdo, Zhifeng Chen, Craig Citro, Greg S. Corrado, Andy Davis, Jeffrey Dean, Matthieu Devin, Sanjay Ghemawat, Ian Goodfellow, Andrew Harp, Geoffrey Irving, Michael Isard, Rafal Jozefowicz, Yangqing Jia, Lukasz Kaiser, Manjunath Kudlur, Josh Levenberg, Dan Mane, Mike Schuster, Rajat Monga, Sherry Moore, Derek Murray, Chris Olah, Jonathon Shlens, Benoit Steiner, Ilya Sutskever, Kunal Talwar, Paul Tucker, Vincent Vanhoucke, Vijay Vasudevan, Fernanda Viégas, Oriol Vinyals, Pete Warden, Martin Wattenberg, Martin Wicke, Yuan Yu, and Xiaoqiang Zheng. "TensorFlow: Large-scale machine learning on heterogeneous systems", 2015. Software available from tensorflow.org.

INDUSTRIAL APPLICABILITY

The invention is applicable wherever a bulky nonwoven fabric with enhanced compressibility and recovery is required—for example in the hygiene industry as various parts of absorbent hygiene products (e.g. baby diapers, incontinence products, female hygiene products, changing pads, etc.) or in healthcare, for example, as a part of protective garments, surgical cover sheets, underlays and other barrier material products. Further uses are also possible in industrial applications, for example as a part of protective garments, in filtration, insulation, packaging, sound adsorption, shoe industry, automotive, furniture, etc. The invention is usable with advantage particularly in applications, where there is a requirement for increased bulkiness, compressibility and recovery of the fabric combined with a requirement for endless fibers.

The invention claimed is:

1. Nonwoven fabric comprising at least one layer, said layer comprising continuous filaments, the continuous filaments comprising at least a first polymeric material and a second polymeric material, the second polymeric material having a melting point that is lower than that of the first polymeric material, wherein the second polymeric material extends in a longitudinal direction of the continuous filaments and forms at least parts of the surfaces of the continuous filaments and the at least one layer of continuous filaments comprises filament-to-filament bonds formed of the second polymeric material, wherein all components of the continuous filaments are arranged across the cross-section of the continuous filaments in a non-crimpable configuration and the nonwoven fabric has a structural softness of at least 80 ($m^4mm^2g^{-2}$), wherein $$\text{Structural softness} = \frac{\text{thickness}}{\text{basis weight}} \times \text{recovery} \times \frac{\text{compressibility}}{\text{basis weight}} \times 10^6$$

wherein thickness is a thickness of the nonwoven fabric in mm, basis weight is the basis weight of the nonwoven structure-fabric in grams per square meter, recovery is the ratio (Tr)/(Ts), wherein (Ts) is an initial thickness of the nonwoven fabric under pre-load of 0.5 kPa and (Tr) is a recovered thickness of the nonwoven fabric measured after a 2.5 kPa load has been applied and afterwards released, compressibility is in mm the difference between the initial thickness of the nonwoven fabric and the thickness of the nonwoven fabric under 5 N load, wherein at least 20% of fibres has the a length of the continuous filaments to a length of the nonwoven fabric ratio higher than 1.2:1.

2. The nonwoven fabric according to claim 1, wherein at least 10% of fibres has the length of the continous filament filaments to the length of the nonwoven fabric ratio higher than 1.5:1.

3. The nonwoven fabric according to claim 2, wherein at least 10% of fibres has the length of the continuous filament filaments to the length of the nonwoven fabric ratio lower than 2.5:1.

4. The nonwoven fabric according to claim 1, wherein the first polymeric material and/or the second polymeric material consists of or comprises as a majority component polymeric material selected from the group consisting of polyesters, polyolefins, polylactic acid, polyester copolymers, polylactide copolymers and blends thereof; and the first polymeric material is different from the second polymeric material.

5. The nonwoven fabric according to claim 1, wherein the continuous filaments have a core/sheath structure, wherein the first polymeric material forms the core and the second polymeric material forms the sheath.

6. The nonwoven fabric according to claim 1, wherein the mass ratio of the first polymeric material to the second polymeric material is 50:50 to 90:10.

7. The nonwoven fabric according to claim 1, wherein the nonwoven fabric has a basis weight of at least 5 gsm.

8. The nonwoven fabric according to claim 1, wherein the filaments have a median fibre diameter of at least 5 microns.

9. The nonwoven fabric according to claim 1, wherein the layer has a void volume of at least 65%.

* * * * *